(12) United States Patent
Eguchi

(10) Patent No.: US 10,945,689 B2
(45) Date of Patent: Mar. 16, 2021

(54) MOBILE RADIATION GENERATOR

(71) Applicant: FUJIFILM Corporation, Tokyo (JP)

(72) Inventor: Koichi Eguchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 61 days.

(21) Appl. No.: 15/706,770

(22) Filed: Sep. 18, 2017

(65) Prior Publication Data

US 2018/0098743 A1    Apr. 12, 2018

(30) Foreign Application Priority Data

Oct. 12, 2016   (JP) .............................. JP2016-200868

(51) Int. Cl.
    *A61B 6/00*    (2006.01)
(52) U.S. Cl.
    CPC ............ *A61B 6/4405* (2013.01); *A61B 6/447* (2013.01)
(58) Field of Classification Search
    CPC ............................. A61B 6/4405; A61B 6/447
    See application file for complete search history.

(56) References Cited

U.S. PATENT DOCUMENTS

| | | | | |
|---|---|---|---|---|
| 1,862,164 A | * | 6/1932 | Sheppard ................ | F16N 13/22 184/35 |
| 3,783,312 A | * | 1/1974 | Schindel ................ | H02K 37/22 310/36 |
| 4,885,950 A | * | 12/1989 | Smith ..................... | F16H 57/12 74/409 |
| 5,110,268 A | | 5/1992 | Sakurai et al. | |
| 5,933,191 A | * | 8/1999 | Ariga ..................... | F16M 11/08 348/373 |

(Continued)

FOREIGN PATENT DOCUMENTS

| | | | | |
|---|---|---|---|---|
| CN | 201192343 | | 2/2009 | |
| GB | 539084 A | * | 8/1941 | ............ A61B 6/447 |

(Continued)

OTHER PUBLICATIONS

Sander et al. Grease Characterization: Are All Greases Lithium Greases?, Lubrication Excellence 2007 Conference Proceedings, pp. 431-437 (Year: 2007).*

(Continued)

*Primary Examiner* — David P Porta
*Assistant Examiner* — Shun Lee
(74) *Attorney, Agent, or Firm* — JCIPRNET

(57) ABSTRACT

A mobile radiation generator includes an arm part on which an irradiation section is mounted. The height of the irradiation section is changed in a case in which the arm part is rotated. A spring generates negative rotational moment in a negative direction where the irradiation section is displaced upward against positive rotational moment that acts on the arm part in a positive direction due to own weight of the irradiation section and the like. A friction mechanism is built in a pillar. In a case in which the magnitude of the positive rotational moment and the magnitude of the negative rotational moment are different from each other, the friction mechanism generates a frictional force acting in a direction opposite to a direction where the arm part is to be rotated due to a difference between the positive rotational moment and the negative rotational moment and cancelling the difference.

24 Claims, 21 Drawing Sheets

(56) References Cited

U.S. PATENT DOCUMENTS

| | | | | |
|---|---|---|---|---|
| 6,163,928 | A | * 12/2000 | Chung | E05D 11/087 16/337 |
| 6,233,785 | B1 | 5/2001 | Tanahashi | |
| 6,763,552 | B1 | * 7/2004 | Kitamura | G06F 1/1616 16/330 |
| 2007/0119025 | A1 | * 5/2007 | Hu | F16M 11/10 16/340 |
| 2007/0138720 | A1 | * 6/2007 | Evans | F16F 1/32 267/162 |

FOREIGN PATENT DOCUMENTS

| | | | |
|---|---|---|---|
| JP | S63266207 | | 11/1988 |
| JP | H03175186 | | 7/1991 |
| JP | H06-26805 | | 4/1994 |
| JP | 2542289 | | 7/1997 |
| JP | H09329127 | | 12/1997 |
| JP | 2000046039 | | 2/2000 |
| JP | 2004313739 | | 11/2004 |
| JP | 2007106885 | | 4/2007 |
| JP | 2007190162 | | 8/2007 |
| JP | 2007211880 | | 8/2007 |
| JP | 2008045677 | | 2/2008 |
| JP | 2011007309 | | 1/2011 |
| JP | 2011214328 | | 10/2011 |
| KR | 20100112441 | | 10/2010 |
| KR | 20100112441 | A * | 10/2010 |
| KR | 20140089254 | | 7/2014 |

OTHER PUBLICATIONS

"Search Report of European Counterpart Application" dated Feb. 27, 2018, p. 1-p. 7.

T&S Corporation, "Xray Imaging Apparatus for Rounds T-WALKERα: Product Guidance on the web site," with partial English translation thereof, Oct. 10, 2008, Available at: http://www.ts-xray.com/case/cat_x_2/entry_423/.

"Search Report of Europe Counterpart Application", dated Oct. 9, 2019, p. 1-p. 4.

"Office Action of Japan Counterpart Application," with English translation thereof, dated Nov. 26, 2019, p. 1-p. 21.

Office Action of Japan Counterpart Application, with English translation thereof, dated Feb. 25, 2020, pp. 1-6.

* cited by examiner

MOBILE RADIATION GENERATOR

CROSS-REFERENCE TO RELATED APPLICATIONS

The present application claims priority under 35 U.S.C. § 119 to Japanese Patent Application No. 2016-200868, filed on Oct. 12, 2016, all of which are hereby expressly incorporated by reference into the present application.

BACKGROUND OF THE INVENTION

1. Field of the Invention

The present invention relates to a mobile radiation generator that is used for radiography.

2. Description of the Related Art

A mobile radiation generator, which is used for radiography, is known in a medical field (for example, see "T&S Co., Ltd., X-ray imaging device for rounds T-WALKERα: product guide on Internet website (URL http://www.ts-xray.com/case/cat_x_2/entry_423/)"). As a mobile radiation generator, there is a cart-type mobile radiation generator in which an irradiation section, an arm part, and a pillar supporting the arm part are mounted on a carriage part capable of traveling. Here, the cart-type mobile radiation generator including the carriage part is simply referred to as a cart. Since the cart can be moved by the travel of the carriage part, the cart is used for radiography performed while the cart goes around hospital rooms where patients are present in a ward.

An irradiation section is mounted on a free end of the arm part, and a base end side of the arm part is mounted on the pillar fixed to the carriage part. Since the arm part is rotatably supported by the pillar, the height of the irradiation section is changed in a case in which the arm part is rotated about the base end side as a fulcrum. The height of the irradiation section is adjusted by the rotation of the arm part.

In the cart disclosed in "T&S Co., Ltd., X-ray imaging device for rounds T-WALKERα: product guide on Internet website (URL http://www.ts-xray.com/case/cat_x_2/entry_423/)", the arm part and the pillar are provided with gas springs. In a case in which a direction where the irradiation section is displaced downward in a vertical direction due to the own weight of the arm part including the irradiation section is referred to as a positive direction, positive rotational moment acts on the arm part in the positive direction. In contrast, the gas springs generate a reaction force against the positive rotational moment. The reaction force generated by the gas springs allows negative rotational moment to act on the arm part in a negative direction opposite to the positive direction. An operating force, which is required in a case in which an operator rotates the arm part in the positive direction, is reduced by the action of the gas springs.

Further, the cart disclosed in "T&S Co., Ltd., X-ray imaging device for rounds T-WALKERα: product guide on Internet website (URL http://www.ts-xray.com/case/cat_x_2/entry_423/)" is provided with a locking mechanism that regulates the rotation of the arm part and a lock operation knob that operates the locking mechanism. The positive rotational moment acting on the arm part is changed according to the rotation position of the arm part. In addition, since the reaction force of the gas spring is also changed according to the degree of contraction of the gas spring, the negative rotational moment is also changed according to the rotation position of the arm part. The min part is stopped at a position where the positive rotational moment and the negative rotational moment are balanced out, but the arm part is rotated in the positive direction or the negative direction at other positions. For this reason, the rotation of the arm part is regulated by the locking mechanism, so that the arm part can be stopped at a desired rotation position.

After an operator rotates the arm part to adjust the height of the irradiation section, the operator operates the lock operation knob to operate the locking mechanism so that the arm part is stopped at the adjusted position.

SUMMARY OF THE INVENTION

In a case in which the height of the irradiation section is adjusted in the cart in the related art disclosed in "T&S Co., Ltd., X-ray imaging device for rounds T-WALKERα: product guide on Internet website (URL http://www.ts-xray.com/case/cat_x_2/entry_423/)", a rotation-locking operation for stopping the arm part at a desired rotation position is required in addition to an operation for adjusting the rotation position by rotating the arm part.

However, since the operations need to be performed with both hands in a case in which the rotation-locking operation is to be performed in addition to an operation for rotating the arm part, there is room for improvement in terms of operability. Specifically, in the case of the rotation-locking operation, an operator needs to operate the lock operation knob with one hand while holding the arm part at a desired rotation position with the other hand. For this reason, both hands are used.

There are many cases in which radiography using the cart is performed for a patient who cannot move to a radiographic room after the cart is carried to the bedside in a hospital room. In a case in which an operator is to adjust the height of the irradiation section, the operator may have to operate the arm part with one hand while supporting the body of a patient on the bed with the other hand. For this reason, there are many requests for the adjustment of the rotation position of the arm part with one hand in the medical settings.

In the cart disclosed in "T&S Co., Ltd., X-ray imaging device for rounds T-WALKERα: product guide on Internet website (URL http://www.ts-xray.com/case/cat_x_2/entry_423/)", an operator can perform an operation for rotating the arm part with one hand but the rotation-locking operation is required to stop the arm part at a desired rotation position. Since both hands need to be used for the rotation-locking operation of "T&S Co., Ltd., X-ray imaging device for rounds T-WALKERα: product guide on Internet website (URL http://www.ts-xray.com/case/cat_x_2/entry_423/)", there is room for improvement in terms of operability in the adjustment of the height of the irradiation section.

A countermeasure that, for example, the rotation and locking of the arm part are performed by electrical means and an operator operates a switch with one hand to stop the arm part at a desired rotation position is also considered for this problem. However, this countermeasure is not preferable in terms of the complication of a structure or costs.

An object of the invention is to provide a mobile radiation generator that allows an operator to adjust the height of an irradiation section with one hand with a simple structure and low costs without using an electrical mechanism.

In order to achieve the object, a mobile radiation generator of the invention includes a carriage part, a pillar, an arm part, a spring, and a friction mechanism. The carriage part includes wheels. The pillar is provided on the carriage part. An irradiation section is mounted on a free end of the arm part, and a base end of the arm part is rotatably supported by the pillar. The position of the irradiation section in a vertical direction is changed in a case in which the arm part is rotated while the base end serves as a base point. The spring generates negative rotational moment in a negative direction where the irradiation section is displaced upward against positive rotational moment that acts on the arm part in a positive direction due to own weight of the arm part and the irradiation section in a case in which a direction where the irradiation section is displaced downward in the vertical direction is prescribed as the positive direction. The friction mechanism that generates a frictional force acting in a direction opposite to a direction where the arm part is to be rotated due to a difference between the positive rotational moment and the negative rotational moment and cancelling a difference between the positive rotational moment and the negative rotational moment in a case in which the magnitude of the positive rotational moment and the magnitude of the negative rotational moment are different from each other.

The friction mechanism preferably includes one set of friction plates and a normal force generating section. The set of friction plates includes a friction plate rotated with the rotation of the arm part and a friction plate disposed so as to face the friction plate to be rotated and not rotated regardless of the rotation of the arm part, and generates a frictional force by contact between friction surfaces of the respective friction plates. The normal force generating section includes a biasing unit applying a biasing force in a direction where the friction surfaces of the set of friction plates are pressed against each other, and generates a normal force on the friction surfaces.

It is preferable that separate materials are used for the arm part and the friction plate and a material having wear resistance higher than wear resistance of the arm part is used for the friction plate.

It is preferable that the friction plates of which the friction surfaces are in contact with each other are made of the same material. It is preferable that the biasing unit includes at least one disc-shaped Belleville spring of which one surface is a convex surface and the other surface is a concave surface.

It is preferable that the biasing unit is a Belleville spring unit that includes a plurality of the Belleville springs arranged so as to be stacked in an axial direction about which the friction plates are rotated.

It is preferable that the Belleville spring unit includes at least one set of Belleville springs having different arrangement postures, the arrangement posture meaning orientation of the convex surface or the concave surface.

It is preferable that the Belleville spring unit includes at least one set of Belleville springs arranged so that the convex surfaces face each other.

It is preferable that the Belleville springs, which are disposed at both ends of the Belleville spring unit, are arranged in a posture where the concave surface faces the outside.

It is preferable that the plurality of Belleville springs having different arrangement postures are mixed in the Belleville spring unit and the numbers of the Belleville springs having the respective arrangement postures are equal to each other.

It is preferable that a cushioning member is interposed between the Belleville spring unit and the friction plate, and the Belleville spring unit applies a biasing force to the friction plate through the cushioning member.

It is preferable that lubricating oil is used as lubricant between the friction surfaces of the friction plates. It is preferable that the lubricating oil is lithium soap grease.

It is preferable that storage portions in which the lubricating oil is stored are formed on the friction surface of at least one friction plate of one set of friction plates. It is preferable that the storage portions are disposed so as to be dispersed in a circumferential direction of the friction surface.

It is preferable that the biasing unit is a Belleville spring unit that includes at least one disc-shaped Belleville spring of which one surface includes a convex surface and the other surface includes a concave surface and includes a plurality of the Belleville springs arranged so as to be stacked in an axial direction about which the friction plates are rotated and the Belleville spring, which is disposed on an end face of the Belleville spring unit facing the friction plate, is arranged in a posture where the concave surface faces the friction plate.

It is preferable that the storage portions are disposed so as to be dispersed on a first circumference facing an outer peripheral edge of the Belleville spring.

It is preferable that the storage portions are also disposed so as to be dispersed on circumferences of a plurality of concentric circles having diameters different from the diameter of the first circumference.

It is preferable that the plurality of concentric circles includes a second circumference that is positioned outside the first circumference and a third circumference that is positioned inside the first circumference.

It is preferable that first storage portions, which are storage portions disposed on the first circumference, are provided on the friction surface of one friction plate of one set of friction plates and second storage portions that are storage portions disposed on the second circumference and third storage portions that are storage portions disposed on the third circumference are provided on the friction surface of the other friction plate thereof.

It is preferable that, on the friction plate where the storage portions are disposed on the second circumference and third circumference, the plurality of storage portions, which are disposed so as to be dispersed on each of the second circumference and the third circumference, are arranged at regular intervals in the circumferential direction and the plurality of storage portions disposed on the second circumference and the plurality of storage portions disposed on the third circumference are disposed in a state in which phases of the storage portions are shifted from each other in the circumferential direction.

It is preferable that the size of the storage portion disposed on the first circumference is larger than the size of the storage portion disposed on the second circumference and the size of the storage portion disposed on the third circumference.

It is preferable that the shape of the storage portion is at least one of a circular shape, the shape of an elongate hole, or the shape of a groove. In a case in which the storage portions are grooves, it is preferable that the grooves are arranged radially on the friction surface.

It is preferable that the mobile radiation generator further comprises a shaft member that is inserted into an opening formed in the friction plate, a supply passage for supplying the lubricating oil to the friction surface is provided in the shaft member, and the supply passage includes an inlet that is formed at one end of the shaft member, a first supply passage that extends from the inlet in an axial direction of the shaft member, and a second supply passage that extends from the first supply passage to an outer peripheral surface of the shaft member and is connected to an outlet formed on the outer peripheral surface at a mounting position of the friction plate in the axial direction.

According to the invention, a mobile radiation generator allows an operator to adjust the height of an irradiation section with one hand without the complication of a structure and an increase in costs.

DESCRIPTION OF THE PREFERRED EMBODIMENTS

First Embodiment

Figure 1:
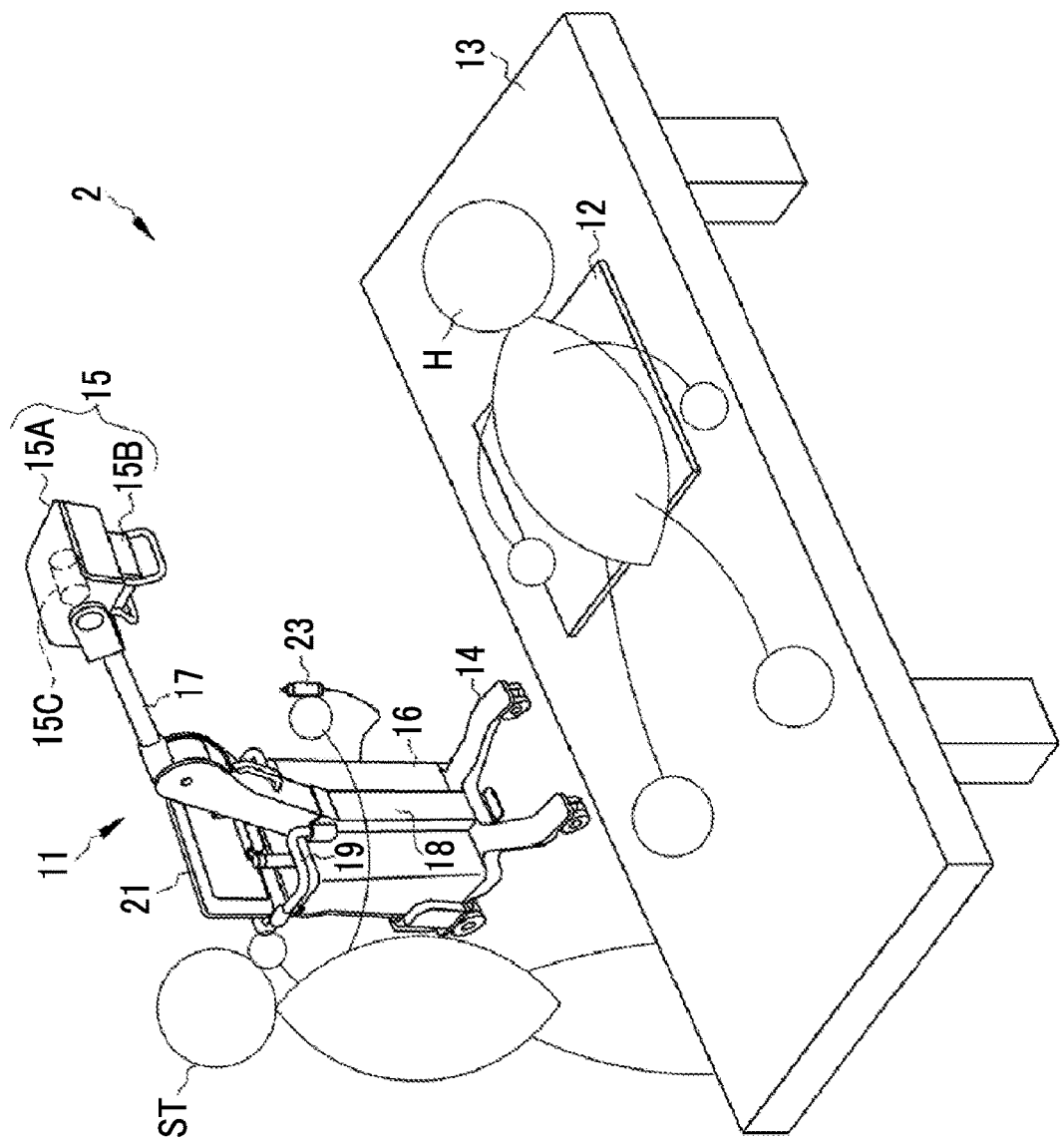
FIG. 1 is a schematic diagram of an X-ray imaging system including a cart.

In FIG. 1, an X-ray imaging system 2 is a radiography system that uses an X-ray as radiation, and includes a cart 11 and an electronic cassette 12. The electronic cassette 12 is a transportable X-ray image detector, and detects an X-ray, which passes through a subject (patient) H, and outputs an X-ray image. The electronic cassette 12 is connected to an imaging control device (not shown), which controls the electronic cassette 12, and a console (not shown), which is in charge of the storage of an X-ray image and display processing, so as to be capable of communicating with the imaging control device and the console in a wireless or wired manner. The electronic cassette 12 is placed on a bed 13 to image, for example, the subject H. In the case of a certain portion to be imaged, positioning depending on a portion to be imaged is performed in such a manner that the subject H holds the electronic cassette 12 in one's arms, or the like.

The cart 11 is a cart-type mobile radiation generator, and generates an X-ray for X-ray imaging. Since the cart 11 includes a carriage part 14 that can travel, a medical staff ST, such as a doctor or a radiographer, can push and move the cart 11 by hand. The cart 11 is used for imaging that is performed while going around the respective hospital rooms in a ward. Further, the cart 11 can be carried to an operating room and can also be used at the time of an operation.

The cart 11 includes an X-ray irradiation section (corresponding to an irradiation section) 15, a body part 16, an arm part 17, a pillar 18, a handle 19, and an operation panel 21. These are mounted on the carriage part 14.

X-Ray Irradiation Section

The X-ray irradiation section 15 includes a radiation source unit 15A that includes an X-ray tube 15C generating an X-ray. An irradiation field limiter (also referred to as a collimator) 15B for limiting the irradiation field of an X-ray, which is generated from the X-ray tube 15C and is applied to the subject H, is mounted on the radiation source unit 15A. The X-ray tube 15C is provided with a filament, a target, a grid electrode, and the like (all of them are not shown). A voltage (tube voltage) is applied between the filament serving as a cathode and the target serving as an anode. The filament generates thermoelectrons depending on the tube voltage. The generated thermoelectrons are emitted to the target. The thermoelectrons, which are generated from the filament, collide with the target, so that the target emits an X-ray. The grid electrode is disposed between the filament and the target, and changes the flow rate of thermoelectrons (tube current), which are emitted to the target from the filament, in accordance with a voltage to be applied.

For example, four shield plates (for example, lead plates) blocking an X-ray are disposed on the respective sides of the quadrangular irradiation field limiter 15B, and a quadrangular emission opening transmitting an X-ray is formed at the central portion of the irradiation field limiter 15B. The size of the emission opening is changed through the change of the position of each shield plate. Accordingly, the irradiation field of an X-ray is changed.

The body part 16 is provided with a radiation source control device that controls the X-ray irradiation section 15, a rechargeable battery that supplies power, and the like. The radiation source control device includes: a voltage generating unit that generates a tube voltage and a voltage to be applied to the grid electrode; and a control unit that controls the operation of the voltage generating unit to control a tube voltage, tube current, and the irradiation time of an X-ray. The radiation source control device and the X-ray irradiation section 15 are connected to each other by a cable that is used to supply a voltage and to transmit a control signal.

Body Part

Figure 2:
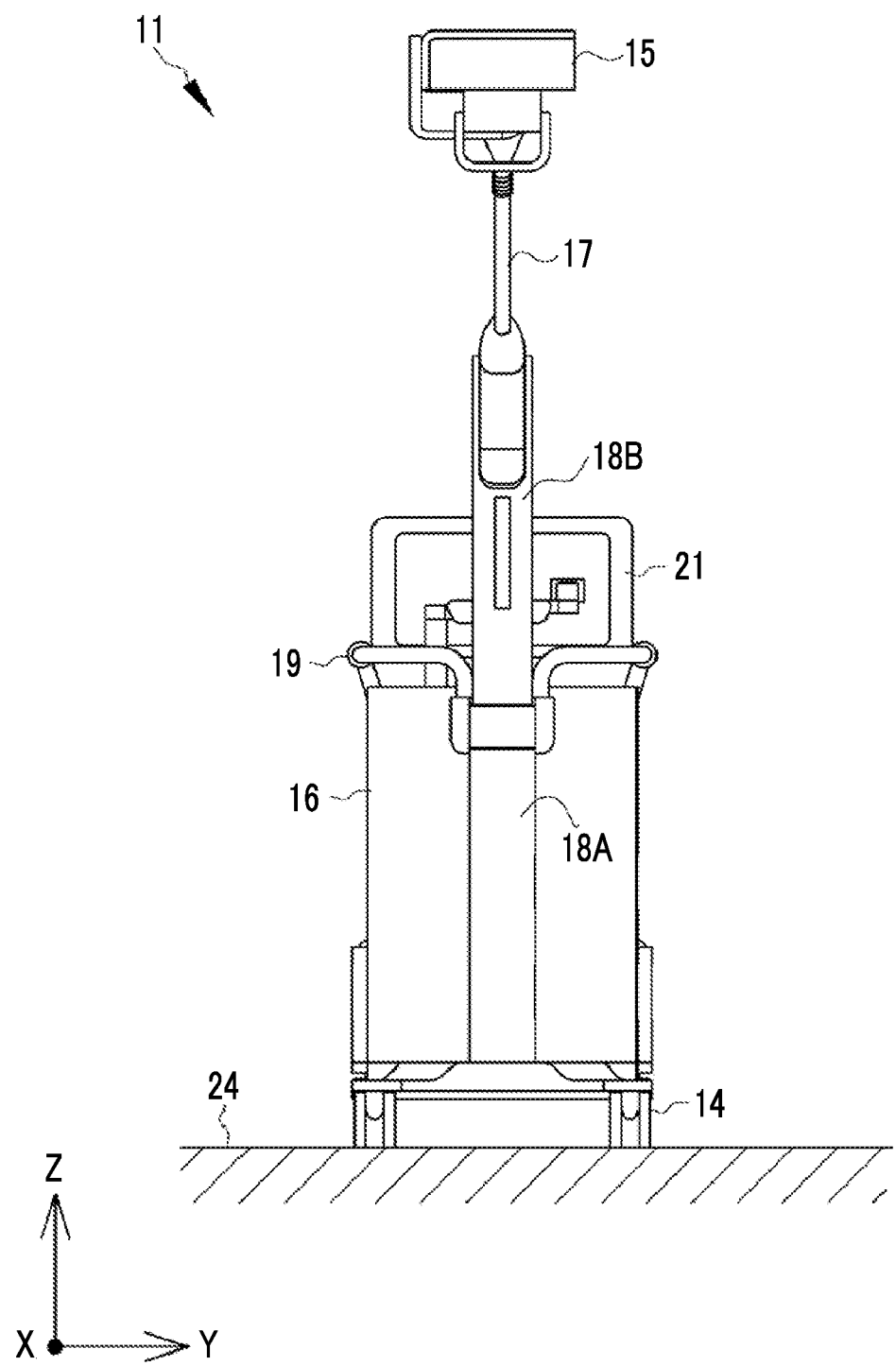
FIG. 2 is a front view of the cart.
Figure 3:
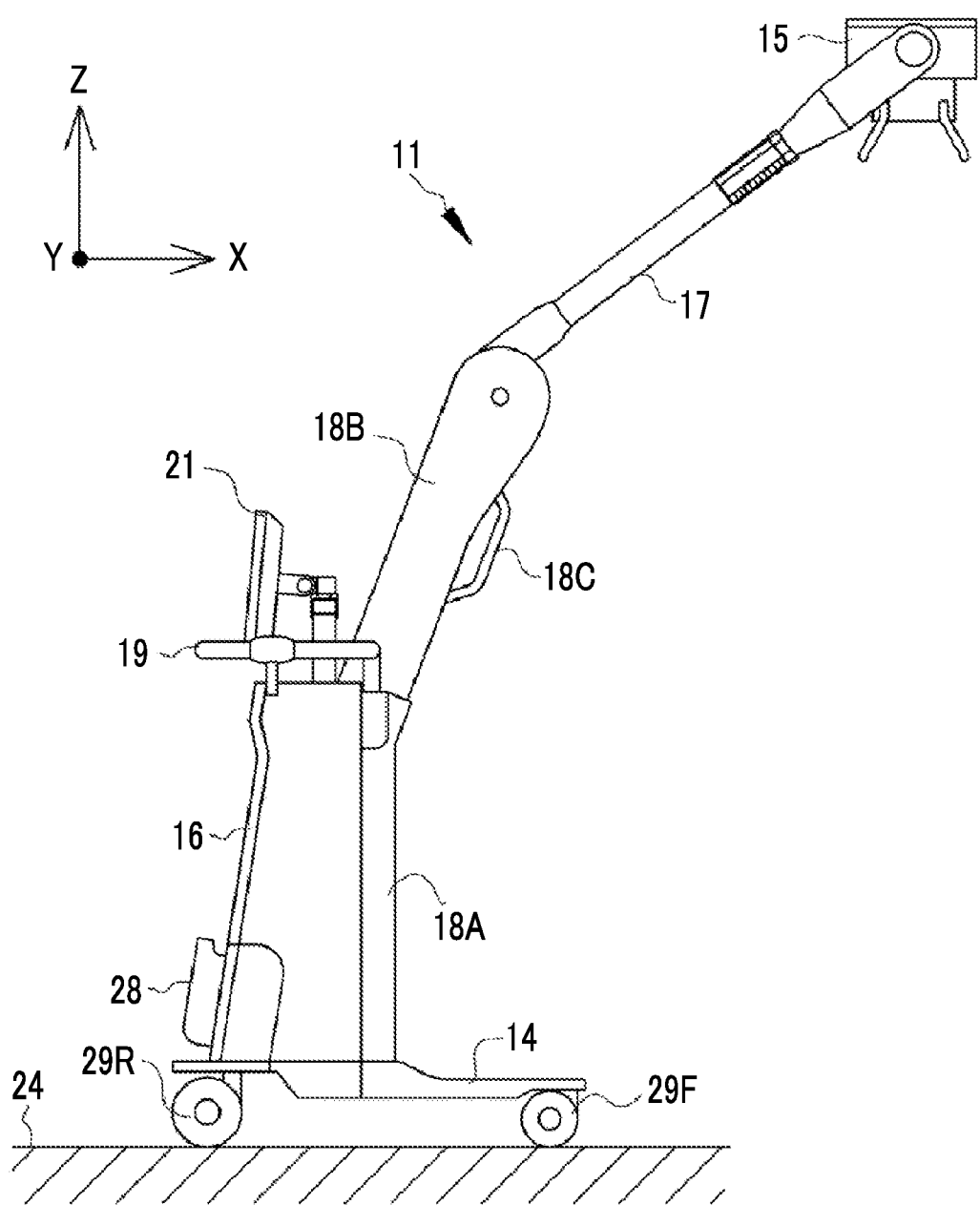
FIG. 3 is a side view of the cart.

The body part 16 is reduced in size and weight, and is formed in a thin shape where a length in a front-rear direction (X-axis direction) is shorter than a length in a width direction (Y-axis direction) as particularly shown in FIGS. 2 and 3. Since the body part 16 is formed in a thin shape, the body part 16 can also enter a narrow space in the hospital room. The length of the body part 16 in the front-rear direction (X-axis direction) is about ⅔ of the length of the carriage part 14 in the front-rear direction. Since the mounting position of the body part 16 on the carriage part 14 is offset rearward, the front portion of the carriage part 14 protrudes to the front side of the body part 16. However, since the height of the carriage part 14 is lower than the height of a leg portion of the bed 13, the carriage part 14 can be made to enter a space below the bed 13. For this reason, in a case in which the front portion of the carriage part 14 is made to enter a gap space below the top board of the bed 13, the front surface of the body part 16 and the bed 13 can be made close to each other.

As shown in FIG. 3, the carriage part 14 includes front wheels 29F and rear wheels 29R corresponding to wheels and the front wheels 29F and the rear wheels 29R rotate about axles thereof, so that the carriage part 14 travels. The front and rear wheels 29F and 29R are formed of casters that independently turn about axes extending in a vertical direction (Z-axis direction) orthogonal to the axles. Since each of the front wheels 29F and the rear wheels 29R are formed of two casters, the carriage part 14 includes a total of four casters of the front and rear wheels 29F and 29R. The two casters forming the rear wheels 29R can also turn independently, the two casters forming the front wheels 29F can also turn independently.

Although not shown, the carriage part 14 is provided with caster locking mechanisms that lock the rotation and turn of the casters. The position and orientation of the carriage part 14 can be fixed during imaging by the caster locking mechanisms.

The body part 16 is provided with the operation panel 21. The operation panel 21 includes an operation unit that is used to operate the X-ray irradiation section 15 and an image display unit that displays the X-ray image detected by the electronic cassette 12. The medical staff ST inputs irradiation conditions of an X-ray (a tube voltage, tube current, irradiation time, and the like) through the operation unit. Further, the body part 16 is provided with the handle 19 that is gripped during the movement of the carriage part 14. Furthermore, a cassette storage portion 28, which stores the electronic cassette 12, is provided on the back surface of the body part 16 as shown in FIG. 3.

An irradiation switch 23, which is used to instruct the X-ray irradiation section 15 to start the irradiation of an X-ray, is connected to the radiation source control device provided in the body part 16. The irradiation switch 23 is, for example, a two-stage pressing switch. The irradiation switch 23 generates a warm-up instruction signal when being pressed by a first stage (half pressed), and generates an irradiation-start instruction signal when being pressed by a second stage (fully pressed).

In a case in which a warm-up instruction signal is input to the radiation source control device, the radiation source control device warms up the filament and starts the rotation of the target at the same time. In a case in which the filament has been completely warmed up and the target reaches a prescribed rotational speed, the warm-up of the filament ends. In a case in which an irradiation-start instruction signal is input to the radiation source control device, the radiation source control device generates a voltage to start the irradiation of an X-ray by the X-ray irradiation section 15. In a case in which irradiation time set as the irradiation conditions has passed, the radiation source control device stops the irradiation of an X-ray.

Pillar and Arm Part

Figure 4:
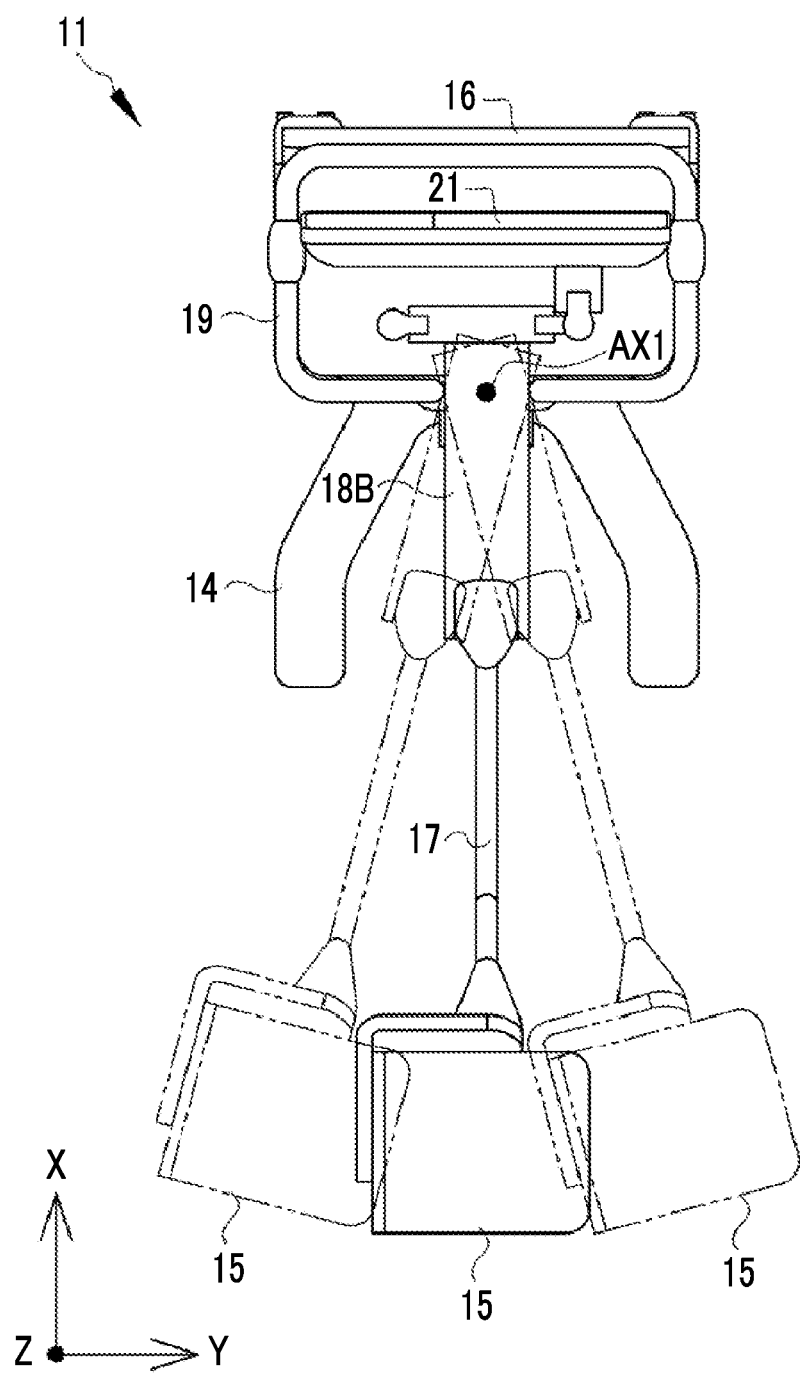
FIG. 4 is a diagram illustrating the rotation of an arm part.

As shown in FIGS. 2 to 4, the X-ray irradiation section 15 is mounted on a free end 17A of the arm part 17 and a base end 17B opposite to the free end 17A is mounted on the pillar 18. The pillar 18 stands on the carriage part 14. As shown in FIG. 2, the pillar 18 is disposed in the middle of the carriage part 14 in the width direction (Y-axis direction). As shown in FIG. 3, the pillar 18 is disposed on the carriage part 14 between the front and rear wheels 29F and 29R in the front-rear direction (X-axis direction).

The pillar 18 includes a first pillar part 18A that is positioned on the lower side in the vertical direction and a second pillar part 18B that is positioned on the upper side. The first pillar part 18A extends vertically upward from the upper surface of the carriage part 14. The longitudinal direction of the first pillar part 18A is parallel to the Z-axis direction. A Z axis corresponds to the vertical direction in a case in which a placement surface 24 on which the carriage part 14 is placed is horizontal. Since a part of the first pillar part 18A is embedded in a recessed portion formed on the front surface of the body part 16, the first pillar part 18A forms a part of the body part 16 from the standpoint of appearance. The lower end of the first pillar part 18A is fixed to the carriage part 14, and the second pillar part 18B is mounted on the upper end of the first pillar part 18A.

As shown in FIG. 3, the second pillar part 18B is inclined toward the front side of the cart 11 with respect to the vertical direction (Z-axis direction). The arm part 17 is mounted on the second pillar part 18B. The base end 17B of the arm part 17 is supported by the upper end of the second pillar part 18B.

As shown in FIG. 4, the base end of the second pillar part 18B is rotatable about a rotation axis AX1, which extends in the Z-axis direction, at the upper end of the first pillar part 18A. The rotation range of the second pillar part 18B is, for example, a range of about 15° at each of left and right positions (shown by a two-dot chain line), that is, 30° in total from an initial position (shown by a solid line) where the longitudinal direction of the second pillar part 18B is parallel to the front-rear direction (X-axis direction) of the cart 11. The rotation angle of the second pillar part 18B can be adjusted to an arbitrary angle in the rotation range. A grip portion 18C, which is gripped during the rotation of the second pillar part 18B, is provided on the front surface of the second pillar part 18B.

Since the first pillar part 18A is fixed to the carriage part 14, the second pillar part 18B rotates about the rotation axis AX1, which extends in the Z-axis direction, with respect to the carriage part 14. Further, the base end 17B of the min part 17 is mounted on the second pillar part 18B. For this reason, the arm part 17 is rotated about the rotation axis AX1 with respect to the carriage part 14 while the base end 17B of the arm part 17 serves as a base point.

Figure 5:
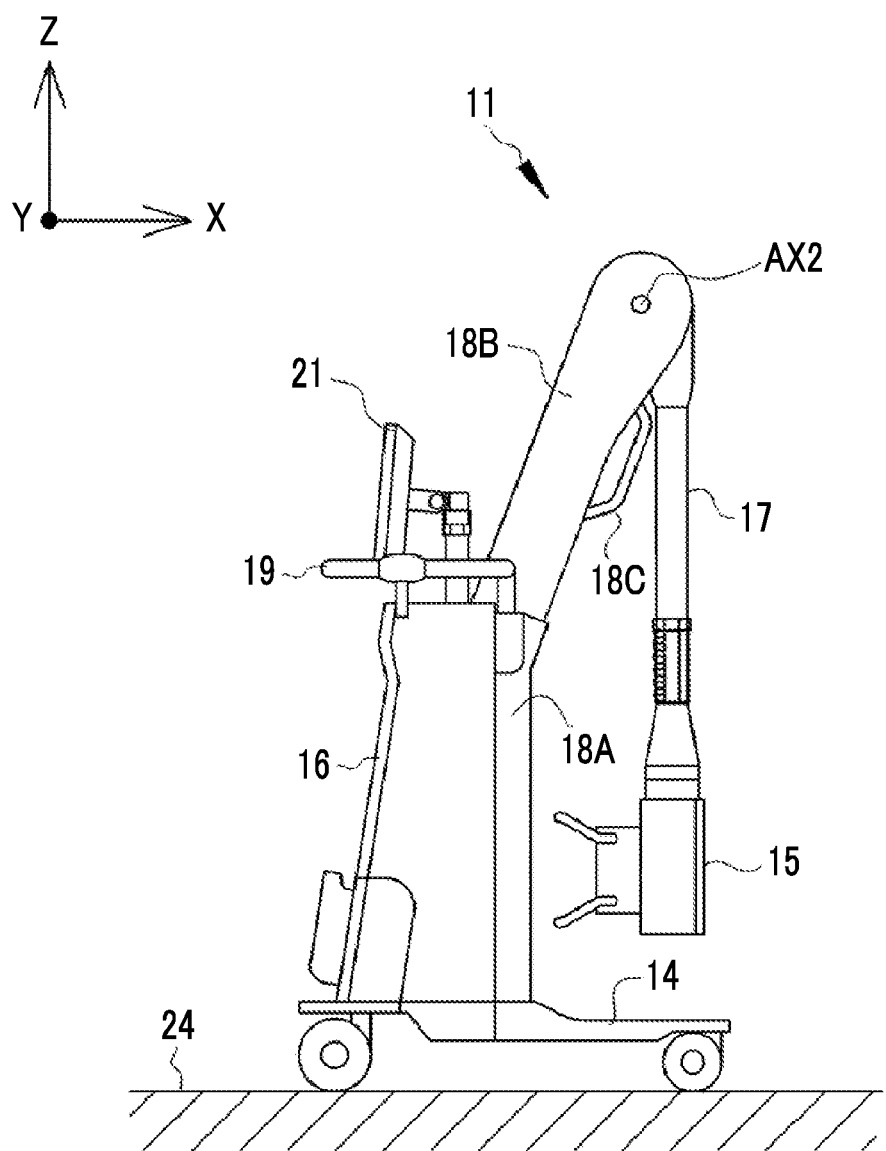
FIG. 5 is a side view of the cart in a state in which the arm part is folded.
Figure 6:
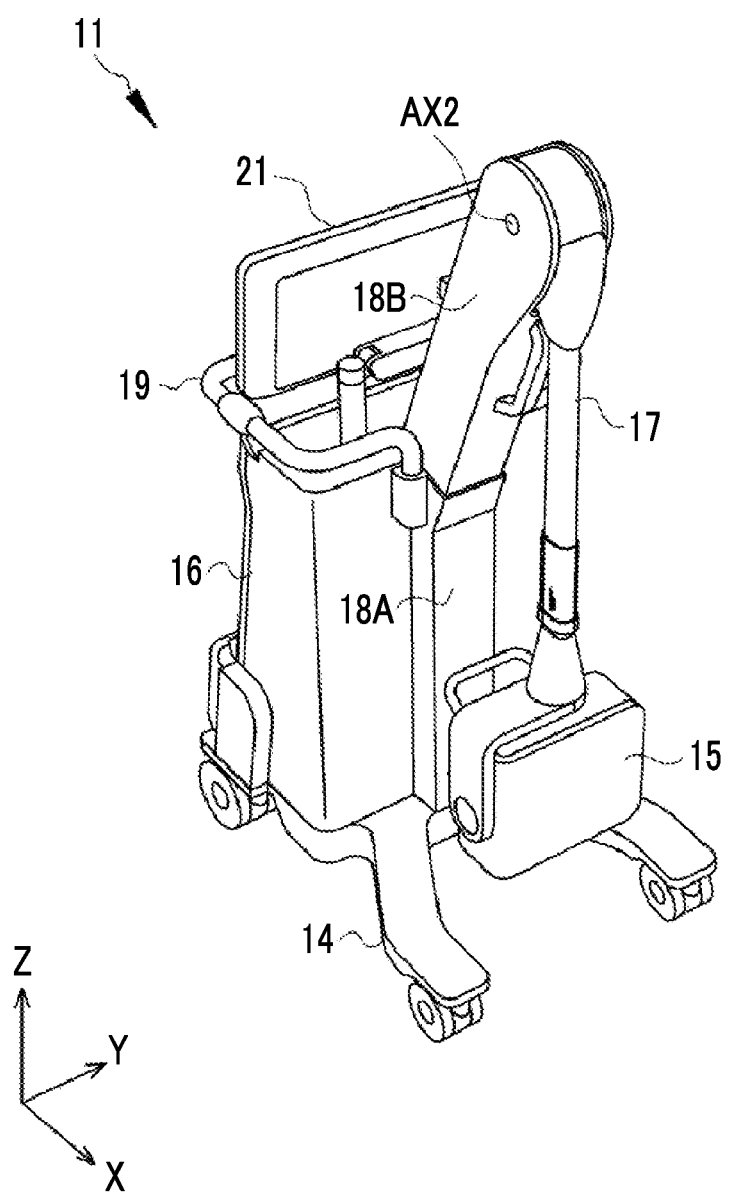
FIG. 6 is a perspective view of the cart in a state in which the arm part is folded.

As shown in FIGS. 5 and 6, the base end 17B of the arm part 17 is supported by the second pillar part 18B, so that the arm part 17 is rotatable about a rotation axis AX2, which extends in the Y-axis direction, serving as a base point. The arm part 17 is rotated about the rotation axis AX2, and is adapted to be folded at a storage position where the front surface of the body part 16 and the X-ray irradiation section 15 face each other. The rotation range of the arm part 17 is a range between the storage position shown in FIGS. 5 and 6 and the upper end position shown in FIG. 3. The position of the X-ray irradiation section 15, which is mounted on the free end 17A, in the vertical direction, that is, the height of the X-ray irradiation section 15 is changed by the rotation of the arm part 17. The height of the X-ray irradiation section 15 can be adjusted to an arbitrary height in the rotation range of the arm part 17.

Further, the arm part 17 can be stopped at an arbitrary rotation position between the upper end position and the storage position around the rotation axis AX2. As described below, the stop of the arm part 17 at the arbitrary rotation position is achieved by the action of a mechanical friction mechanism 50 (see FIG. 12), which is built in a connecting portion between the base end of the arm part 17 and the second pillar part 18B, without the use of an electrical mechanism.

Rotation Mechanism and Friction Mechanism of Arm Part

Figure 7:
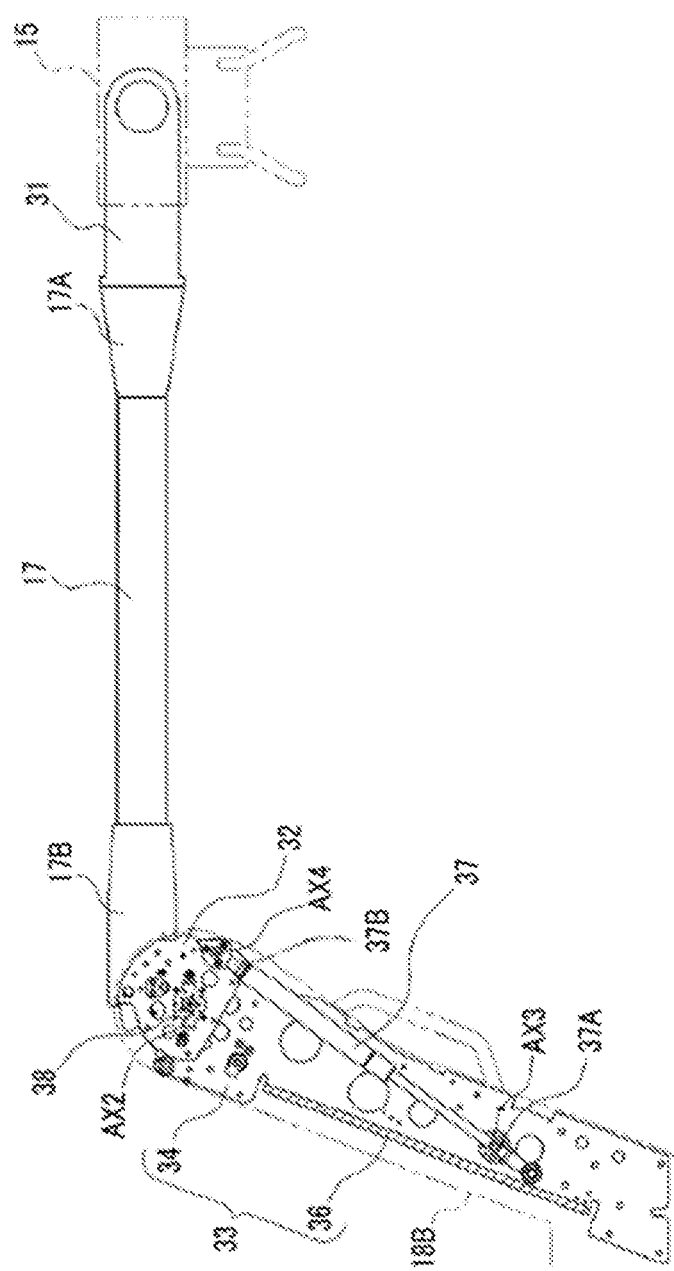
FIG. 7 is a side view of a rotation mechanism and a friction mechanism of the arm part.
Figure 8:
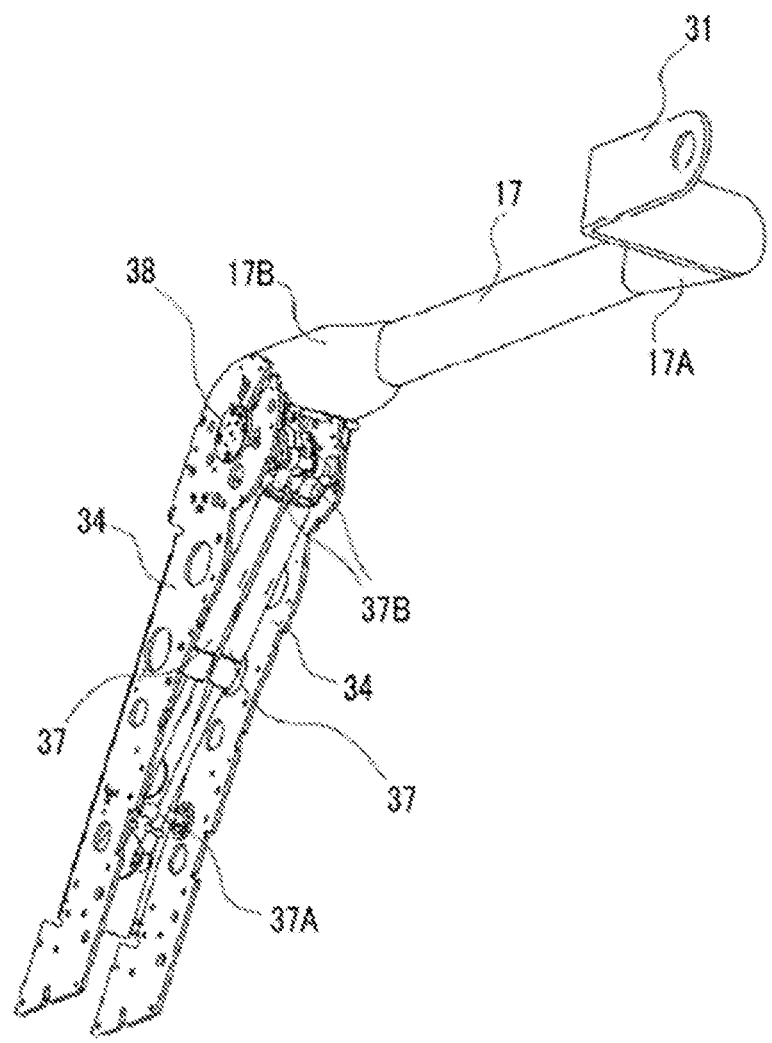
FIG. 8 is a perspective view of the rotation mechanism and the friction mechanism of the arm part.

As shown in FIGS. 7 and 8, a holding portion 31 where the X-ray irradiation section 15 is mounted and held is provided at the free end 17A of the arm part 17. The X-ray irradiation section 15 is mounted on the free end 17A of the arm part 17 through the holding portion 31. A mounting part 32, which is used to mount the arm part 17 on the second pillar part 18B, is provided at the base end 17B of the arm part 17.

The second pillar part 18B includes an exterior member and a frame member 33 that extends in the longitudinal direction of the second pillar part 18B and is provided in the exterior member. Since the frame member 33 is made of, for example, aluminum, the frame member 33 is reduced in weight. The frame member 33 includes a pair of frame plates 34 that is disposed at intervals in the width direction (Y-axis direction) and a back plate 36 that connects the frame plates 34. The mounting part 32 of the arm part 17 is received between the respective frame plates 34, and is rotatably supported by a shaft member 38. The rotation axis AX2 corresponds to an abstract concept representing the geometric center of rotation, and the center of the substantive shaft member 38 in a radial direction corresponds to the rotation axis AX2 of the arm part 17. The shaft member 38 itself is substantially a fixed shaft that does not rotate.

Here, in regard to the rotational direction of the arm part 17, a direction where the height of the X-ray irradiation section 15 in the vertical direction is moved down is prescribed as a positive direction and a direction opposite to the positive direction is prescribed as a negative direction. In FIG. 7, a clockwise direction about the rotation axis AX2 is a positive direction and a counterclockwise direction about the rotation axis AX2 is a negative direction. As shown in FIG. 3, even at an upper end of the rotation range of the arm part 17, the arm part 17 is in a posture where the free end 17A on which the X-ray irradiation section 15 is mounted is inclined forward. For this reason, positive rotational moment, which allows the arm part 17 to be rotated in the positive direction, acts on the arm part 17 due to the own weight of the arm part 17 and the X-ray irradiation section 15.

The frame member 33 is provided with two gas springs 37. One end portion 37A of each gas spring 37 is mounted on each frame plate 34, and the other end portion 37B of each gas spring 37 is mounted on the mounting part 32 of the arm part 17. The end portion 37A is rotatable about a rotation axis AX3, and the end portion 37B is rotatable about a rotation axis AX4. The gas spring 37 is a spring that uses a reaction force based on elasticity obtained in a case in which gas filled in a cylinder is compressed as well known. Since the gas spring 37 is mounted in a state in which the gas spring 37 contracts in a compression direction where the filled gas is compressed, the gas spring 37 always generates a reaction force in a stretching direction.

The end portion 37B of the gas spring 37 is disposed at the mounting part 32 so as to be offset from the rotation axis AX2 toward the free end 17A of the arm part 17. For this reason, the gas spring 37 generates negative rotational moment, which acts on the arm part 17 in a negative direction where the X-ray irradiation section 15 is displaced upward in the vertical direction, by a reaction force in the stretching direction against the positive rotational moment that is generated due to the own weight of the arm part 17 and the like and acts in the positive direction. The strong rotation of the arm part 17 in the positive direction can be suppressed by the action of the gas springs 37, and a load required in a case in which the medical staff ST as an operator rotates the arm part 17 in the negative direction to raise the X-ray irradiation section 15 can be reduced by the action of the gas springs 37.

Figure 9:
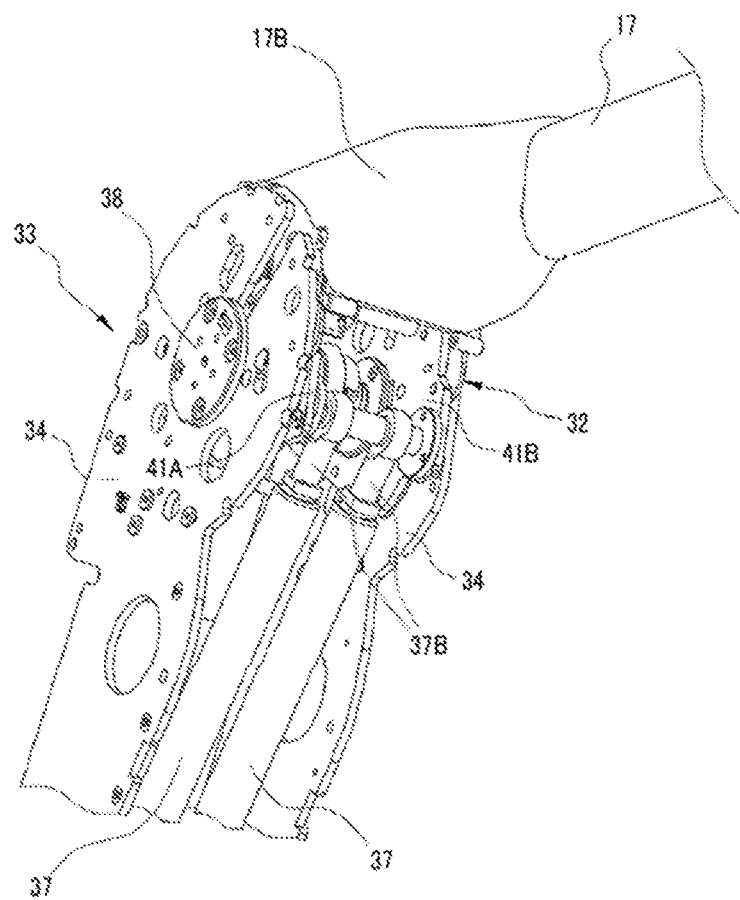
FIG. 9 is an enlarged view of main parts of FIG. 8.
Figure 10:
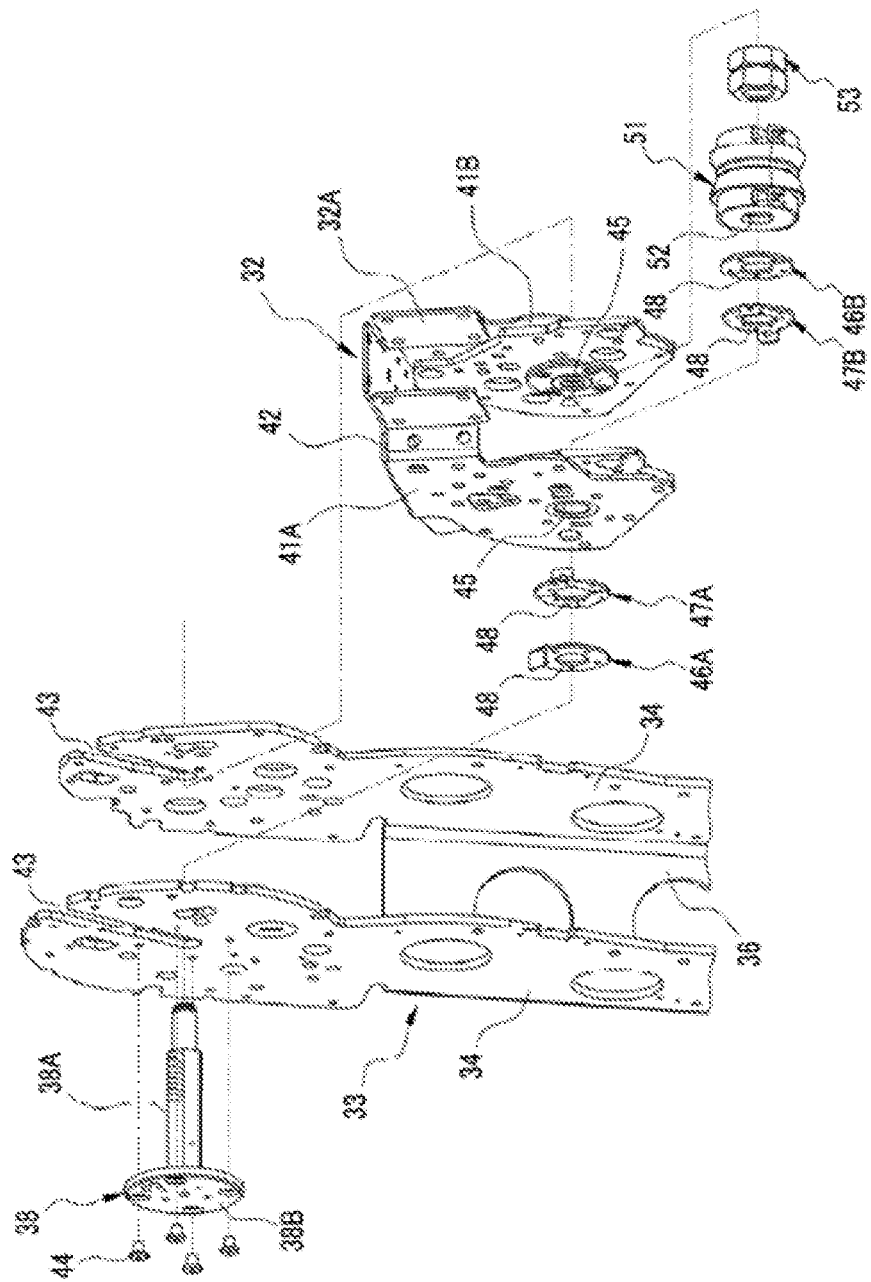
FIG. 10 is an exploded perspective view of the friction mechanism.

As shown in FIGS. 9 and 10, the mounting part 32 includes two side plates 41A and 41B that are disposed at intervals in the width direction (Y-axis direction) and a connecting portion 42 that connects the two side plates 41A and 41B. An interval between the two side plates 41A and 41B is a width that allows the total width of the side plates 41A and 41B to be received in the interval between the two frame plates 34 of the frame member 33. Reference numeral 32A denotes joints that are to be joined to a frame (not shown) of the arm part 17. As in the case of the frame member 33, the mounting part 32 is reduced in weight since the mounting part 32 is made of, for example, aluminum.

As shown in FIG. 10, the side plates 41A and 41B are provided with shaft holes 45 into which the shaft member 38 is inserted. On the other hand, the two frame plates 34 are provided with bearing slits 43 that function as bearings for the shaft member 38. The shaft member 38 is mounted in a state in which the shaft member 38 is inserted into the bearing slits 43 of the two frame plates 34 and the shaft holes 45 of the two side plates 41A and 41B. The shaft member 38 includes a shaft portion 38A and a large-diameter portion 38B that is provided at one end portion of the shaft portion 38A and has a diameter larger than the diameter of the shaft portion 38A. The large-diameter portion 38B is fixed to one frame plate 34 by screws 44, so that the shaft member 38 is fixed. The mounting part 32 is rotatably mounted on the shaft member 38. The arm part 17 is rotated about the rotation axis AX2 by the rotation of the mounting part 32.

Sets of friction plates 46 and 47 are provided on both sides of the side plate 41A in the axial direction of the shaft member 38. One set of friction plates 46 and 47 generates a frictional force by the contact between friction surfaces of the friction plates 46 and 47. Shaft holes 48 are formed in these friction plates 46 and 47, and the friction plates 46 and 47 are mounted in a state in which the shaft member 38 is inserted into the shaft holes 48. The friction plate 47 is a rotating friction plate that is rotated about the rotation axis AX2 with the rotation of the arm part 17, and the friction plate 46 is a fixed friction plate that does not rotate about the rotation axis AX2 regardless of the rotation of the arm part 17. Here, in a case in which the fixed friction plate 46 and the rotating friction plate 47 do not need to be distinguished from each other, the fixed friction plate 46 and the rotating friction plate 47 are merely referred to as the friction plates 46 and 47. In a case in which the rotating friction plate 47 and the fixed friction plate 46 need to be distinguished from each other, the friction plates 46 and 47 are referred to as the fixed friction plate 46 and the rotating friction plate 47.

The two rotating friction plates 47 are mounted on both sides of the side plate 41A, and are fixed not to be rotated by rotation stop. Since the side plate 41A is rotated in a case in which the arm part 17 is rotated, the two rotating friction plates 47 also rotate with together with the side plate 41A. Further, the respective friction plates 46 and 47 are mounted so as to be movable in the axial direction.

Each of the friction plates 46 and 47 is made of a material having wear resistance higher than the wear resistance of the arm part 17. A material having high wear resistance is heavy. As described above, aluminum is used as the material of the arm part 17 so that the arm part 17 is reduced in weight. The arm part 17 becomes heavy in a case in which the arm part 17 is made of a material having high wear resistance. For this reason, the friction plates 46 and 47 are formed of members separate from the arm part 17 for the improvement of the wear resistance of the friction plates 46 and 47 and a reduction in the weight of the arm part 17. The material of each of the friction plates 46 and 47 is specifically phosphor bronze.

Further, the outer diameters of the friction plates 46 and 47 are relatively small so that the friction plates 46 and 47 are built in the second pillar part 18B. In a case in which a large frictional force is to be generated by friction plates of which the areas of the friction surfaces are small like the friction plates 46 and 47, a large load is applied to the friction surfaces of the friction plates in comparison with friction plates each of which has a large diameter and a large area of the friction surface. In this case, the degree of deterioration of each of the friction plates 46 and 47 is high and the deterioration rate of each of the friction plates 46 and 47 is also high. For this reason, a material having high wear resistance is used to suppress the deterioration of the friction plates 46 and 47 as much as possible.

Furthermore, the friction plates 46 and 47, which are in contact with each other, are made of the same material. In a case in which the hardness of the friction plate 46 is different from the hardness of the friction plate 47, the friction plate having a lower hardness is likely to be cut. Since the friction plates are made of the same material, the wear of the friction plates 46 and 47 is suppressed. Since wear causes a frictional force to be reduced, it is possible to stabilize a frictional force, which is generated by the friction plates 46 and 47, with time by suppressing wear.

Moreover, lubricant is applied to the friction surfaces of the friction plates 46 and 47 to suppress the wearing of the friction surfaces. It is preferable that lubricating oil, which is liquid lubricant, is used as the lubricant, and it is more preferable that lithium soap grease is used as the lubricant. In a case in which solid lubricant, such as molybdenum disulfide, is used, a frictional force generated by the friction plates 46 and 47 is more likely to be destabilized with time in comparison with a case in which lubricating oil is used. It is thought that the reason for this is that an interval between the friction surfaces of the friction plates 46 and 47 is changed due to the crush of particles of the solid lubricant with time. In a case in which lubricating oil is used, a frictional force is likely to be stabilized with time without such a concern that an interval between the friction surfaces of the friction plates 46 and 47 may be changed. It is continued that lithium soap grease among them exhibits good performance.

Here, in a case in which the two rotating friction plates 47 are to be distinguished from each other, the rotating friction plate 47 disposed between the side plate 41A and the frame plate 34 is referred to as a rotating friction plate 47A and the rotating friction plate 47 disposed between the side plate 41A and the side plate 41B is referred to as a rotating friction plate 47B. Further, in a case in which the two fixed friction plates 46 are to be distinguished from each other, the fixed friction plate 46 disposed so as to face the rotating friction plate 47A is referred to as a fixed friction plate 46A and the fixed friction plate 46 disposed so as to face the rotating friction plate 47B is referred to as a fixed friction plate 46B.

The fixed friction plate 46A is mounted on the frame plate 34, and is fixed not to be rotated by rotation stop. On the other hand, the fixed friction plate 46B is disposed outside the rotating friction plate 47A, that is, between the rotating friction plate 47A and the side plate 41B. Unlike in the case of the shaft hole 48 of the other friction plate, the cross section of the shaft hole 48A of the fixed friction plate 46B orthogonal to the axial direction has a D-cut shape. The cross section of a portion, on which the fixed friction plate 46B is mounted, of the shaft portion 38A of the shaft member 38 orthogonal to the axial direction has a D shape. The fixed friction plate 46B is fixed to the shaft portion 38A not to be rotated with respect to the shaft portion 38A by the engagement between the shaft hole 48A and the shaft portion 38A.

A normal force generating section 51 is disposed between the fixed friction plate 46B and the side plate 41B. The normal force generating section 51 applies a biasing force in a direction where the friction surfaces of the respective sets of friction plates 46 and 47 are pressed against each other to generate a normal force on the friction surfaces. The normal force generating section 51 is also mounted on the shaft portion 38A of the shaft member 38. The normal force generating section 51 includes an insertion hole 52 into which the shaft portion 38A is inserted. A part of the insertion hole 52 has a D-cut shape as in the case of the shaft hole 48A of the fixed friction plate 46B. As in the case of the fixed friction plate 46B, the normal force generating section 51 is fixed to the shaft portion 38A not to be rotated with respect to the shaft portion 38A by the engagement between the insertion hole 52 having a D-cut shape and the shaft portion 38A having a D-shaped cross section.

In the normal force generating section 51, nuts 53 are provided at an end portion of the side plate 41B. The nuts 53 are to adjust the normal force that is generated on the friction plates 46 and 47 by the normal force generating section 51.

Figure 11:
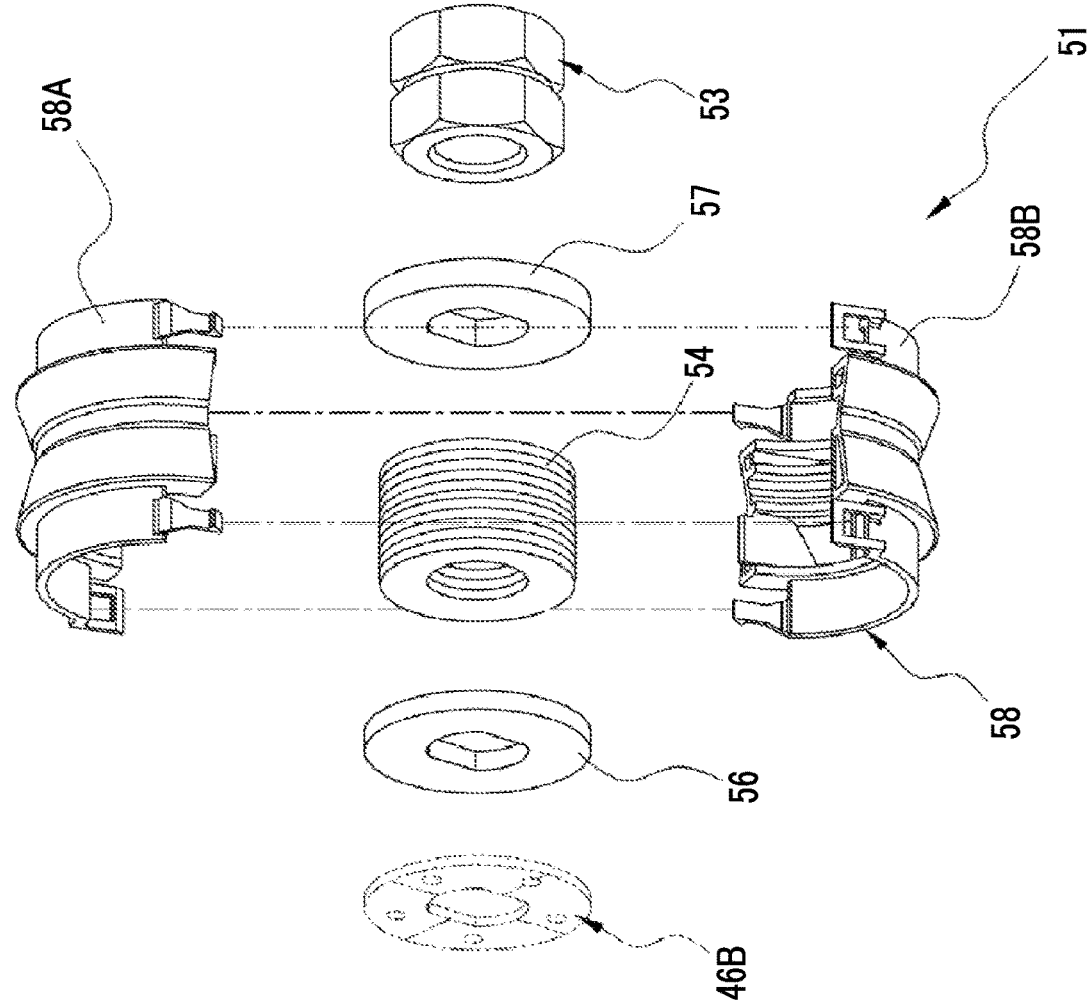
FIG. 11 is an exploded perspective view of a normal force generating section.
Figure 12:
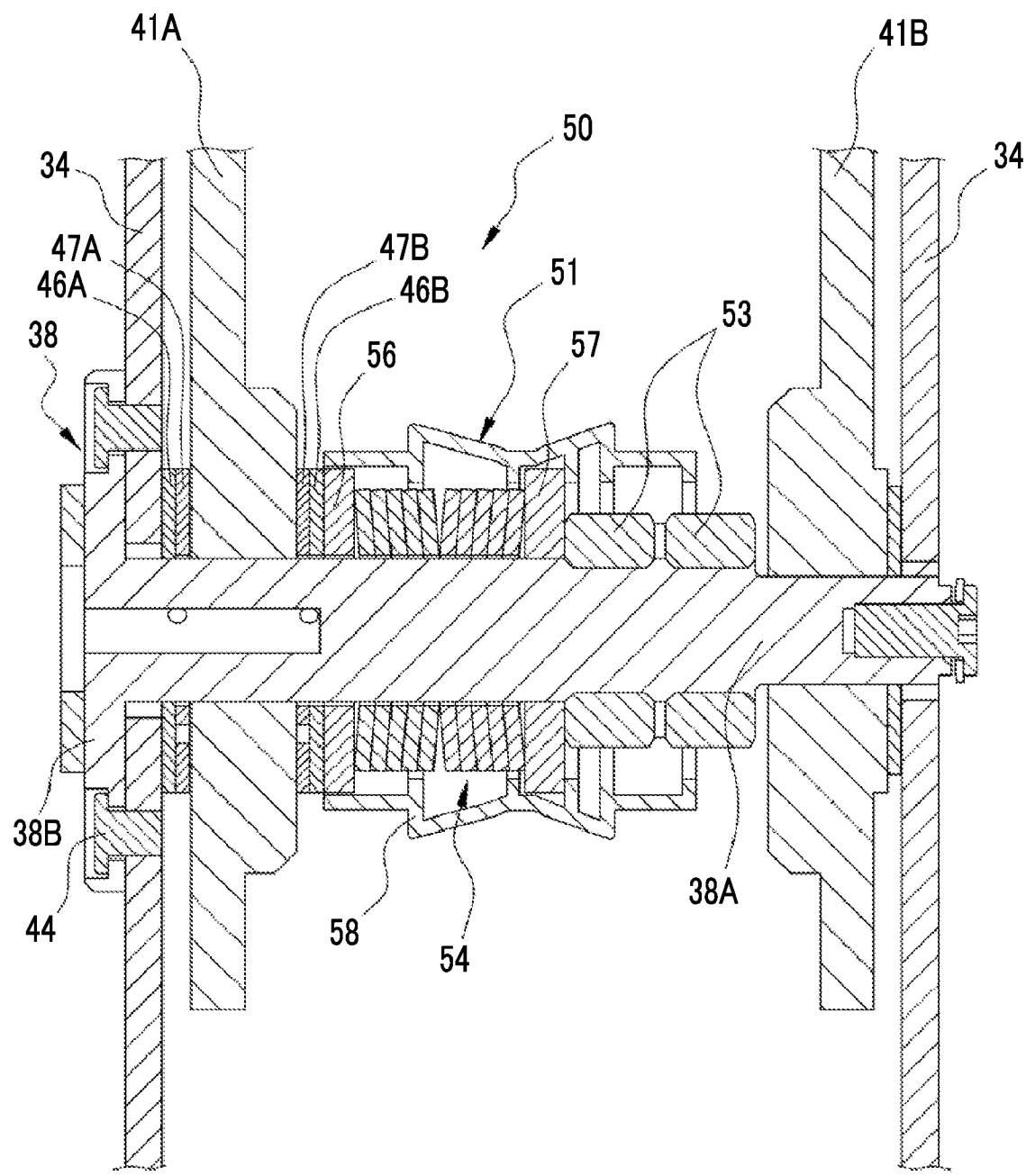
FIG. 12 is a cross-sectional view of the friction mechanism.

As shown in FIGS. 11 and 12, the normal force generating section 51 includes a Belleville spring unit 54 that functions as a biasing unit, cushioning plates 56 and 57, a case 58, and the nuts 53. The case 58 has a structure that is divided into two upper and lower members, that is, an upper case member 58A and a lower case member 58B, and receives the Belleville spring unit 54 and the cushioning plates 56 and 57. The Belleville spring unit 54 applies a biasing force in a direction where the friction surfaces of the friction plates 46 and 47 are pressed against each other. In a case in which the friction surfaces of the friction plates 46 and 47 are pressed against each other, a normal force is generated on the friction surfaces.

The Belleville spring unit 54 includes a plurality of Belleville springs 61. A load is applied to the Belleville spring unit 54, in a direction where the Belleville spring unit 54 contracts, in accordance with a force for tightening the nuts 53. Since the Belleville spring unit 54 is elastically deformed so as to contract as a load depending on the force for tightening the nuts 53 is increased, a reaction force generated by the Belleville spring unit 54 is also increased. As the number of Belleville springs 61 of the Belleville spring unit 54 is increased, the Belleville spring unit 54 can increase a reaction force.

Figure 13A:
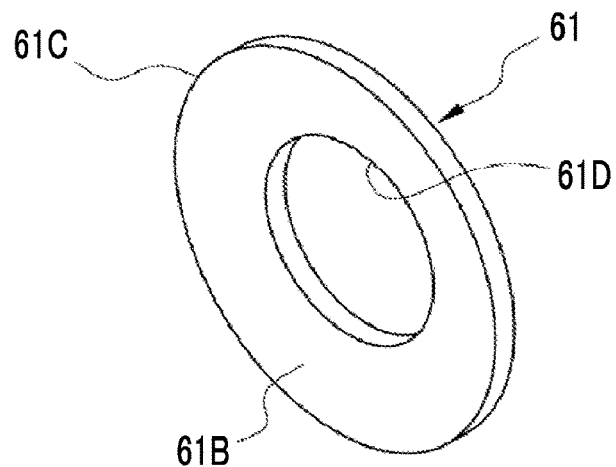
FIG. 13A is a perspective view of a Belleville spring.
Figure 13B:
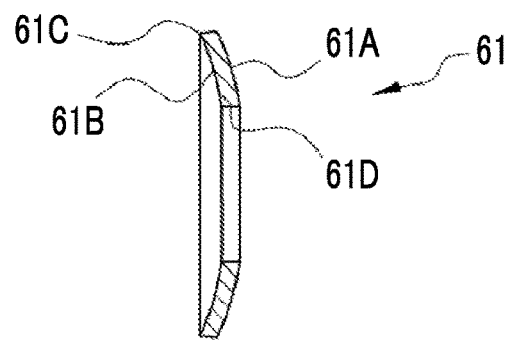
FIG. 13B is a cross-sectional view of the Belleville spring.
Figure 13C:
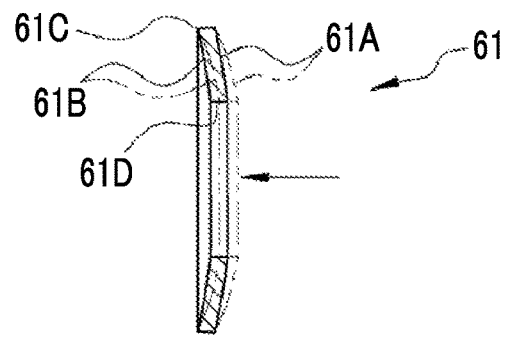
FIG. 13C is a cross-sectional view of the Belleville spring that is elastically deformed by an applied external force.

As shown in FIGS. 13A to 13C, the Belleville spring 61 is a disc-shaped spring of which one surface is a convex surface 61A and the other surface is a concave surface 61B. Reference numeral 61C denotes an outer peripheral edge of the concave surface 61B. The Belleville spring 61 is provided with a shaft hole 61D into which the shaft portion 38A is inserted. In a case in which a load is applied to the Belleville spring 61 in a direction (axial direction) orthogonal to the radial direction from an initial state shown in FIG. 13B, the Belleville spring 61 is elastically deformed as shown in FIG. 13C so that the convex surface 61A becomes concave and generates a reaction force based on elasticity. The Belleville springs 61 can save a space and generate a large normal force in comparison with a coil spring.

As shown in FIG. 12, the plurality of Belleville springs 61 of the Belleville spring unit 54 are arranged so as to be stacked in the axial direction of the shaft portion 38A. The cushioning plates 56 and 57 (corresponding to a cushioning member) are disposed at both ends of the Belleville spring unit 54 in the axial direction. The cushioning plate 56 is disposed between the Belleville spring unit 54 and the fixed friction plate 46B. The cushioning plate 57 is disposed between the Belleville spring unit 54 and the nuts 53. The cushioning plates 56 and 57 and the Belleville spring unit 54 are mounted so as to be movable in the axial direction of the shaft portion 38A as in the cases of the friction plates 46 and 47.

In a case in which the nuts 53 are tightened in a state in which the end face of the Belleville spring unit 54 is in contact with the cushioning plate 56, the Belleville spring unit 54 is moved in a direction where the Belleville spring unit 54 presses the cushioning plate 56. In a case in which the Belleville spring unit 54 is moved, a pressing force is applied to the respective sets of friction plates 46 and 47 through the cushioning plate 56. In a case in which the nuts 53 are further tightened and the Belleville spring unit 54 reaches the limit of movement, the Belleville springs 61 are elastically deformed and the Belleville spring unit 54 contracts in the axial direction. The force for tightening the nuts 53 is adjusted at the time of manufacture so that a reaction force generated by the Belleville spring unit 54 reaches a predetermined set value.

The Belleville spring unit 54 is biased on the basis of elasticity in a direction where the friction surfaces of the friction plates 46 and 47 are pressed against each other. For this reason, even in a case in which the friction surfaces of the friction plates 46 and 47 are worn, the Belleville spring unit 54 is stretched in the axial direction and applies a biasing force. Accordingly, a reduction in the normal force is suppressed.

Figure 14:
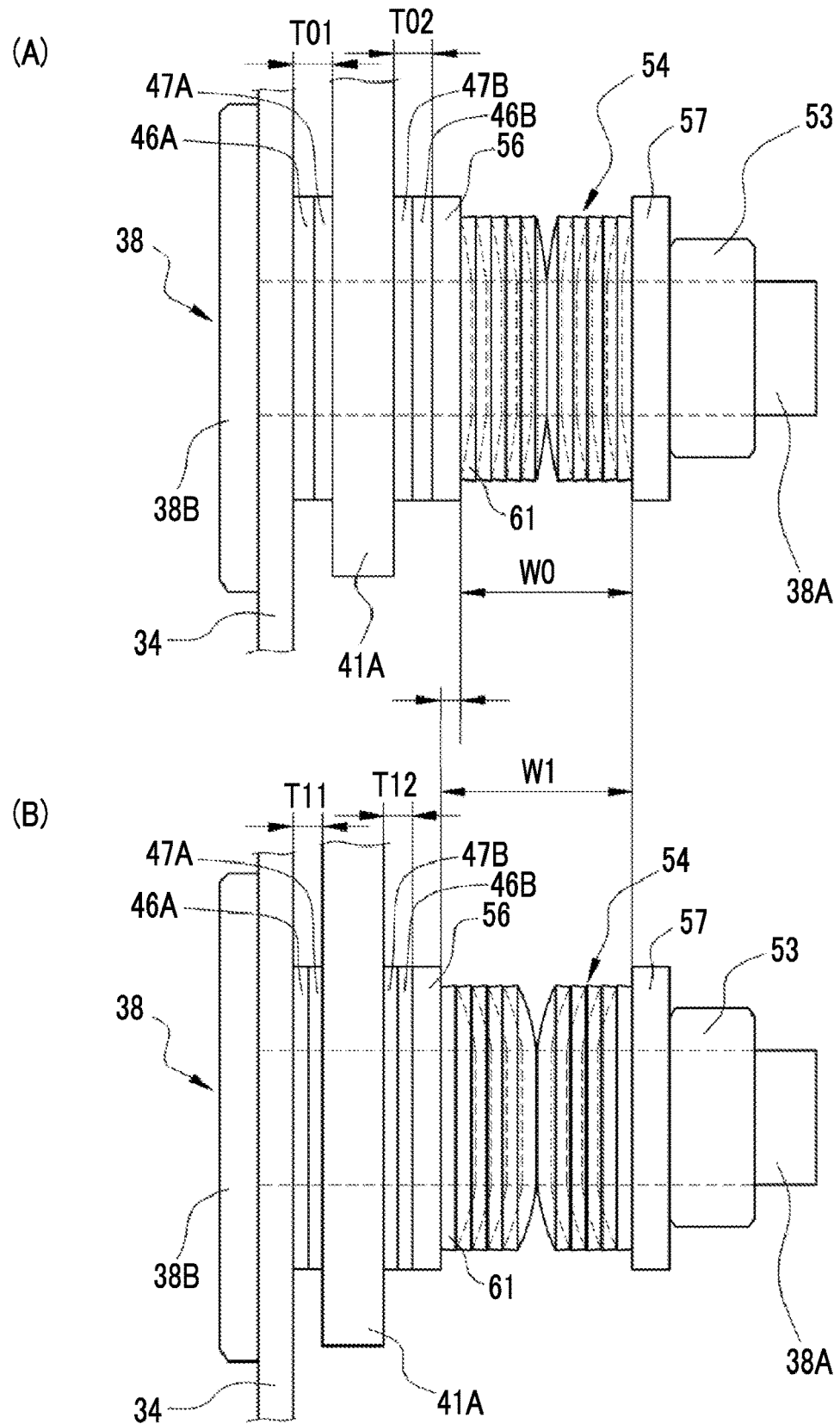
FIG. 14 illustrates the state (A) of the friction mechanism before the wear of a friction plate and the state (B) of the friction mechanism after the wear of a friction plate.

For example, in FIG. 14, it shows an initial state (A) in which the friction surfaces of the friction plates 46 and 47 are not worn, and a state (B) in which the wear of the friction plates 46 and 47 has proceeded due to use. The nuts 53 are tightened in the initial state (A) shown in FIG. 14 so that the degree of contraction of the Belleville spring unit 54 corresponds to an initial value at the time of manufacture. The width of the Belleville spring unit 54 in the initial state in the axial direction is denoted by W0 and the thicknesses of the sets of friction plates 46 and 47 are denoted by T01 and T02, respectively.

In a case in which the wear of the friction plates 46 and 47 proceeds, the thicknesses of the friction plates 46 and 47 are reduced and the thicknesses of the sets of friction plates 46 and 47 are changed to T11 and T12, respectively, as shown in the state (B) of FIG. 14. Even though the thicknesses of the friction plates 46 and 47 are reduced as described above, the Belleville spring unit 54 is stretched in the axial direction by an elastic force so as to have a width W1 that is larger than the width W0. Accordingly, since the friction surfaces of the friction plates 46 and 47 are pressed against each other, a reduction in a normal force is suppressed even though the friction surfaces are worn.

In FIG. 12, the cushioning plate 56 functions as a cushioning member that is interposed between the Belleville spring unit 54 and the fixed friction plate 46B. The biasing force of the Belleville spring unit 54 is applied to the fixed friction plate 46B through the cushioning plate 56. Since the Belleville spring 61 has the shape of a disc of which one surface is convex, the contact surface of the Belleville spring 61, which is in contact with the cushioning plate 56, is not a flat surface. If the Belleville spring 61 is made to be in direct contact with the fixed friction plate 46B, the contact area between the fixed friction plate 46B and the Belleville springs 61 is small in comparison with a case in which the contact surface of the Belleville spring is a flat surface. Accordingly, stress is concentrated. As a result, uneven wear is likely to occur on the friction surfaces of the fixed friction plate 46B and the rotating friction plate 47B, which causes a frictional force to be reduced. For this reason, in a case in which the cushioning plate 56 of which the contact surface being in contact with the fixed friction plate 46B is a flat surface is interposed, stress generated on the fixed friction plate 46B is dispersed. Accordingly, a reduction in a frictional force caused by uneven wear is suppressed.

Further, the plurality of Belleville springs 61 having different arrangement postures are mixed in the Belleville spring unit 54 of this embodiment. The arrangement posture means the orientation of the convex surface 61A or the concave surface 61B. In this embodiment, five Belleville springs 61 corresponding to a left half and five Belleville springs 61 corresponding to a right half are arranged so that the concave surfaces 61B of the respective Belleville springs 61 face the outside in FIG. 12. Accordingly, the arrangement postures of the Belleville springs 61 are different from each other.

Furthermore, in a case in which at least one set of Belleville springs 61 having different arrangement postures is included as in the Belleville spring unit 54 of this embodiment, the spring constant of the entire Belleville spring unit 54 can be made small in comparison with a case in which all Belleville springs 61 have the same arrangement posture. Since a spring constant (N/m) is the variation of an elastic force (reaction force) with respect to the unit displacement of a spring, a change in the elastic force (reaction force) of the Belleville spring unit 54 corresponding to the displacement in the axial direction can be suppressed by a reduction in a spring constant.

That is, in a case in which wear occurs on the friction plates 46 and 47 as shown in FIG. 14, the Belleville spring unit 54 is stretched in the axial direction and the width of the Belleville spring unit 54 is changed. Even though the width of the Belleville spring unit 54 is changed as described above, a change in the reaction force of the Belleville spring unit 54 can be suppressed in a case in which a spring constant is set to be small. Accordingly, a frictional force, which is generated by the friction plates 46 and 47, is stabilized with time.

In order to obtain an effect of making a spring constant small, at least one set of Belleville springs 61 having different arrangement postures may be included and the position of one set of Belleville springs 61 in the axial direction may be an arbitrary position.

Further, in the Belleville spring unit 54 of this embodiment, the numbers of the plurality of Belleville springs 61 having different arrangement postures (in this embodiment, the number of the Belleville springs corresponding to the right half and the number of the Belleville springs corresponding to the left half) are equal to each other, and are five, respectively. Since the numbers of Belleville springs 61 having different arrangement postures are set to be equal to each other, the permanent deformation of only the Belleville springs 61, which have the same arrangement posture and of which the number is smaller, is prevented. In a case in which the numbers of Belleville springs 61 having different arrangement postures are different from each other, the degree of deformation of the Belleville springs 61, which have the same arrangement posture and of which the number is smaller, is relatively large and permanent deformation occurs on only the Belleville springs 61, which have the same arrangement posture and of which the number is not smaller, is relatively large. The permanent deformation of the Belleville spring 61 causes the reaction force of the Belleville spring unit 54 to be reduced. Since the numbers of Belleville springs 61 having different arrangement postures are set to be equal to each other, a reduction in a reaction force can be suppressed.

Furthermore, each of the Belleville springs 61, which are disposed at both ends of the Belleville spring unit 54 in the axial direction of the shaft portion 38A, is arranged in a posture where the concave surface 61B faces the outside (that is, the each of concave surfaces 61B of the Belleville springs 61 faces each end of both ends of the Belleville spring unit 54 in the axial direction). Since each of the Belleville springs 61, which are disposed at both ends of the Belleville spring unit 54, is arranged in this posture, the following merits are obtained in comparison with a case in which each of the Belleville springs 61, which are disposed at both ends of the Belleville spring unit 54, is disposed in a posture where the convex surface 61A faces the outside.

First, since the outer peripheral edge 61C of the concave surface 61B of the Belleville spring 61, which is disposed on an end face, is in contact with the cushioning plate 56, a pressing force at the outer peripheral edge 61C becomes relatively large on the friction surface. In a case in which the Belleville spring 61 is disposed so that the convex surface 61A faces the outside, the contact portion of the Belleville spring 61, which is in contact with the cushioning plate 56, is positioned near a peak at which the protruding length of the convex surface 61A is maximum and which is positioned at the center. Accordingly, a pressing force is relatively large at the center of the friction surface.

For this reason, considering rotational moment around an axis of the friction surface, in a case in which the concave surface 61B is disposed so as to face the outside and the outer peripheral edge 61C distant from the center of rotation positioned at the center of the Belleville spring is used as the point of application of force, rotational moment around the axis can be made large in comparison with a case in which the center of the Belleville spring is used as the point of application of force. Second, in a case in which the cushioning plate 56 is pressed at the outer peripheral edge 61C of the concave surface 61B, the contact area is increased in comparison with a case in which the cushioning plate 56 is pressed at the center of the convex surface 61A. Accordingly, the concentration of stress on the cushioning plate 56 and the friction plates 46 and 47 can also be suppressed.

Further, two Belleville springs 61, which are disposed in the middle of the Belleville spring unit 54, are arranged so that the convex surfaces 61A face each other. Accordingly, it is easy to confirm the degree of tightening of the nuts 53 at the time of assembly. The reason for this is that the interval between the Belleville springs 61 is reduced as the degree of tightening of the nuts 53 is increased in a case in which the nuts 53 are tightened to make the Belleville spring unit 54 contract in the axial direction. In a state in which the convex surfaces 61A face each other, a gap between two Belleville springs 61, which face each other, is relatively large at the outer periphery of the Belleville spring 61. Since it is easy to visually confirm the size of the gap as described above, it is easy to confirm whether or not the degree of tightening of the nuts 53 at the time of assembly is appropriate.

The friction plates 46 and 47 and the normal force generating section 51 form the friction mechanism 50 that stops the arm part 17 at an arbitrary rotation position in the entire rotation range between the upper end position and the storage position. The friction surfaces of the friction plates 46 and 47 are in contact with each other and a normal force is generated on the friction surfaces by the action of the normal force generating section 51. For this reason, a frictional force opposite to the rotational direction of the arm part 17 is generated on the friction surfaces of the rotating friction plate 47 and the fixed friction plate 46 in a case in which the rotating friction plate 47 is to be rotated by the rotation of the arm part 17.

It is necessary to balance rotational moment, which acts on the arm part 17, out to stop the arm part 17. For this reason, to stop the arm part 17 at an arbitrary rotation position, a frictional force generated by the friction mechanism 50 is set to a magnitude that allows the rotational moment acting on the arm part 17 to be balanced out in the entire rotation range of the arm part 17.

Figure 15A:
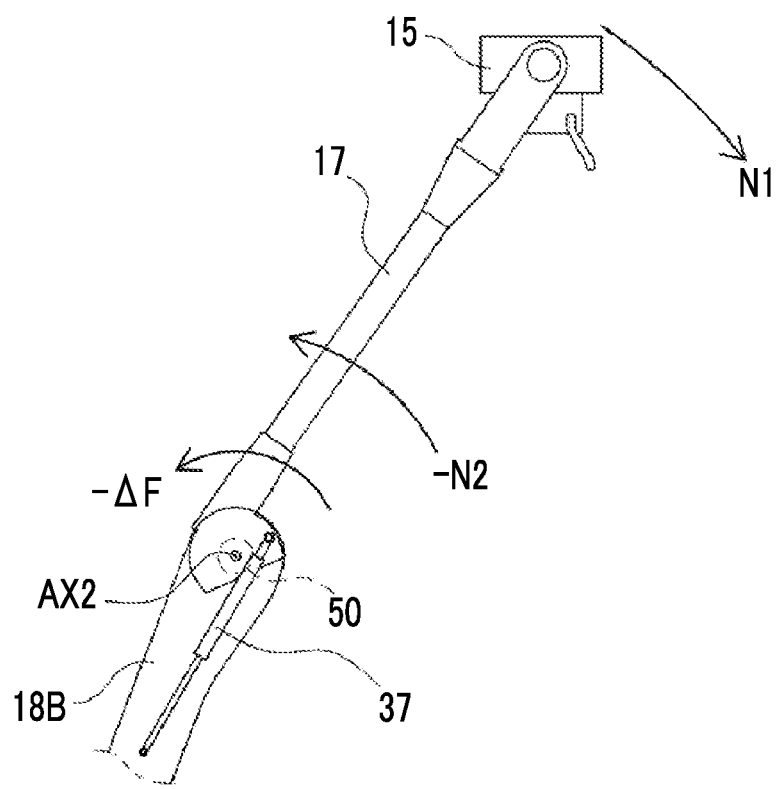
FIG. 15A is a diagram illustrating rotational moment acting on the arm part that is in an upper end position.
Figure 15B:
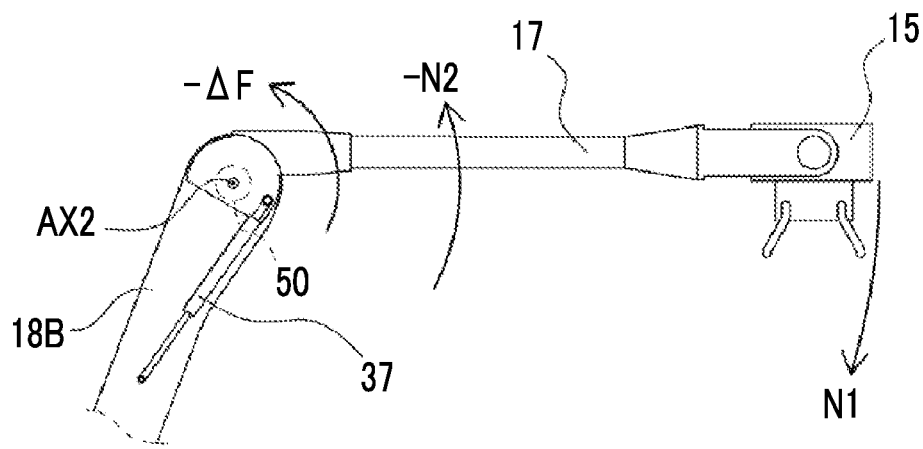
FIG. 15B is a diagram illustrating rotational moment acting on the arm part that is in a horizontal state.
Figure 15C:
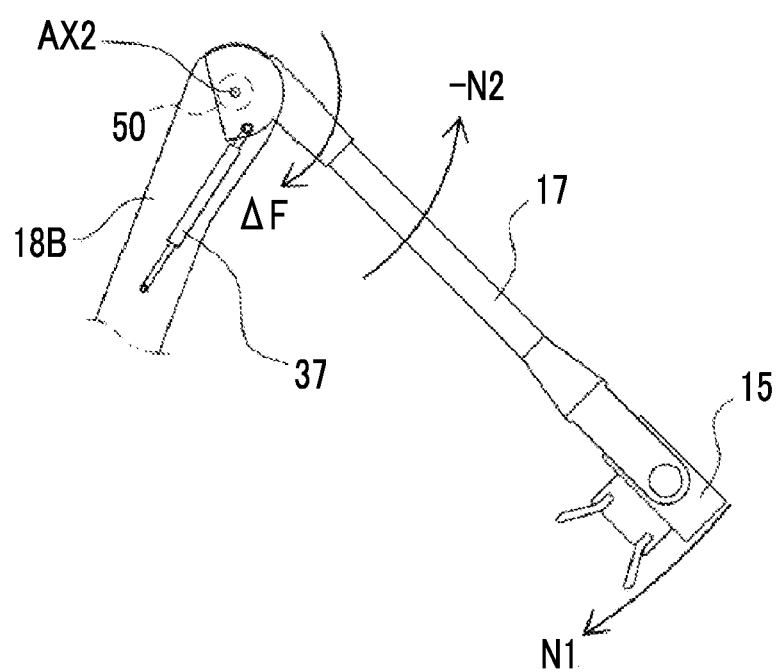
FIG. 15C is a diagram illustrating rotational moment acting on the arm part that is in a position lower than the horizontal state.

As shown in FIGS. 15A to 15C, rotational moment acting on the arm part 17 includes positive rotational moment N1 that is generated in the positive direction by the own weight of the arm part 17 and the weight of the X-ray irradiation section 15 and negative rotational moment N2 that is generated in the negative direction on the basis of the elastic force of the gas springs 37. In FIGS. 15A and 15B, a minus sign is given to N2 since the direction of N2 is opposite to the direction of N1.

The magnitudes of all the positive rotational moment N1 and the negative rotational moment N2 are changed according to a rotation position. The positive rotational moment N1 is maximum in a state in which the arm part 17 is stretched in a horizontal direction as shown in FIG. 15B, and is then reduced. The negative rotational moment N2 is maximum at the storage position where the degree of contraction of the gas springs 37 is maximum (an elastic force is also maximum) as shown in FIG. 15C, and is reduced toward the upper end position.

In a case in which the magnitude of the positive rotational moment N1 and the magnitude of negative rotational moment N2 are equal to each other and are not different from each other, that is, a case in which "N1−N2=0" is satisfied, the arm part 17 is stopped. However, since the magnitude of the positive rotational moment N1 and the magnitude of negative rotational moment N2 are different from each other at other positions, the arm part 17 is not stopped.

The friction mechanism 50 generates a frictional force $\Delta F$ that acts in a direction opposite to the rotational direction of the arm part 17 due to a difference between the positive rotational moment N1 and the negative rotational moment N2 to cancel a difference between the positive rotational moment N1 and the negative rotational moment N2 in a case in which the magnitude of the positive rotational moment N1 and the magnitude of negative rotational moment N2 are different from each other.

In FIG. 15A, at the upper end position, the positive rotational moment N1 is larger than the negative rotational moment N2 that acts on the basis of the reaction force of the gas springs 37 (N1>N2). For this reason, a difference between the positive rotational moment N1 and the negative rotational moment N2 satisfies "N1−N2=ΔF". To cancel a difference ΔF between the positive rotational moment N1 and the negative rotational moment N2, the friction mechanism 50 generates a frictional force −ΔF, which has the same magnitude as ΔF, in the negative direction opposite to the positive direction in which the arm part 17 is to be rotated by ΔF. Accordingly, a difference between the positive rotational moment N1 and the negative rotational moment N2 is cancelled and rotational moment acting on the arm part 17 is balanced out, so that the arm part 17 is stopped at the upper end position.

Since the gas springs 37 contract at a position where the arm part 17 is in a horizontal state as shown in FIG. 15B in comparison with the upper end position, the magnitude of the negative rotational moment N2 is increased. However, since the positive rotational moment N1 is maximum in the horizontal state, the positive rotational moment N1 is larger than the negative rotational moment N2 in a state shown in FIG. 15B as in FIG. 15A (N1>N2). For this reason, a difference between the positive rotational moment N1 and the negative rotational moment N2 satisfies "N1−N2=ΔF". To cancel a difference ΔF between the positive rotational moment N1 and the negative rotational moment N2, the friction mechanism 50 generates a frictional force −ΔF, which has the same magnitude as ΔF, in the negative direction opposite to the positive direction in which the arm part 17 is to be rotated by ΔF. Accordingly, a difference between the positive rotational moment N1 and the negative rotational moment N2 is cancelled and rotational moment acting on the arm part 17 is balanced out, so that the arm part 17 is stopped in the horizontal state.

In a case in which the arm part 17 is further rotated in the positive direction from the horizontal state as shown in FIG. 15C, the positive rotational moment N1 is reduced. On the other hand, since the degree of contraction of the gas springs 37 is further increased, a reaction force is also further increased. Accordingly, the negative rotational moment N2 is increased. FIG. 15C shows a state in which the magnitude of the positive rotational moment N1 and the magnitude of the negative rotational moment N2 are reversed, that is, "N1<N2" is satisfied. In this state, a difference between the positive rotational moment N1 and the negative rotational moment N2 satisfies "N1−N2=−ΔF". To cancel a difference −ΔF between the positive rotational moment N1 and the negative rotational moment N2, the friction mechanism 50 generates a frictional force ΔF, which has the same magnitude as −ΔF, in the positive direction opposite to the negative direction in which the arm part 17 is to be rotated by −ΔF. Accordingly, a difference between the positive rotational moment N1 and the negative rotational moment N2 is cancelled and rotational moment acting on the arm part 17 is balanced out, so that the arm part 17 is stopped.

The positive rotational moment N1 is changed according to the own weight of the arm part 17 including the X-ray irradiation section 15, the length of the arm part 17, and the rotation position of the arm part 17. On the other hand, the negative rotational moment N2 is changed according to the performance of the gas springs 37 and the degree of contraction of the gas springs 37 that depend on the rotation position of the arm part 17. For this reason, the magnitude of a difference between the positive rotational moment N1 and the negative rotational moment N2 is also changed according to these. A frictional force generated by the friction mechanism 50 is determined according to the maximum value of a difference between the positive rotational moment N1 and the negative rotational moment N2. Accordingly, the arm part 17 can be stopped at an arbitrary rotation position in the rotation range of the arm part 17.

Although not shown, the cart 11 is provided with a storage position locking mechanism that locks the rotation of the arm part 17 at the storage position of the arm part 17. The storage position locking mechanism is used in, for example, a case in which the cart 11 is to be moved to a ward from a standby position, and the like. Since the storage position locking mechanism is provided, the arm part 17 can be reliably fixed at the storage position so that the arm part 17 is not rotated carelessly during the movement of the cart 11.

Action

The action of the above-mentioned structure will be described below. In a case in which the medical staff ST is to perform imaging, the medical staff ST makes the carriage part 14 of the cart 11 travel to carry the cart 11 to a hospital room in which imaging is to be performed.

As shown in FIG. 1, in the hospital room, the medical staff ST moves the cart 11 or adjusts the height and the irradiation direction of the X-ray irradiation section 15 to position the X-ray irradiation section 15. First, the medical staff ST positions the electronic cassette 12 in accordance with a portion to be imaged of a subject H (see FIG. 1) lying on the bed 13. After that, the medical staff ST positions the X-ray irradiation section 15 so that the electronic cassette 12 and the X-ray irradiation section 15 face each other.

The positioning of the X-ray irradiation section 15 may also be performed with one hand while, for example, the medical staff ST supports the body of a patient with one hand. The height of the X-ray irradiation section 15 is adjusted by the rotation of the arm part 17. Positive rotational moment N1 acts on the arm part 17 on the basis of the own weight of the arm part 17, but negative rotational moment N2 also acts on the arm part 17 on the basis of the reaction force of the gas springs 37. Since the gas springs 37 are provided, an operating force for rotating the arm part 17 in the positive direction is reduced. Accordingly, it is easy for the medical staff ST to raise the X-ray irradiation section 15 with one hand.

Then, while rotating the arm part 17 with one hand, the medical staff ST adjusts the X-ray irradiation section 15 to a desired height. After the medical staff ST can adjust the X-ray irradiation section 15 to a desired height, the medical staff ST releases one's hand from the arm part 17 at the rotation position of the arm part 17. As shown in FIGS. 15A to 15C, the friction mechanism 50 generates a frictional force ΔF for cancelling a difference between the positive rotational moment N1 and the negative rotational moment N2 even in a case in which the positive rotational moment N1 and the negative rotational moment N2 acting on the arm part 17 are different from each other. For this reason, the medical staff ST can stop the arm part 17 at an arbitrary rotation position by only releasing one's hand from the arm part 17 without performing an operation for locking the rotation position or the like. For this reason, unlike in the related art, the medical staff ST does not need to perform an operation for locking the rotation position of the arm part 17 while holding the arm part 17 at a desired rotation position with one hand. Accordingly, the medical staff ST can adjust the height of the X-ray irradiation section 15 with one hand.

A mechanism for stopping the rotation position is realized using the mechanical friction mechanism 50. For this reason, a structure is not complicated and a low cost can be realized in comparison with a case in which an electrical mechanism is used.

Further, in the cart 11 of this embodiment, as described above, separate members are used as the arm part 17 and the friction plates 46 and 47, a lightweight material (aluminum in this embodiment) is used for the arm part 17, and a material (phosphor bronze in this embodiment) having wear resistance higher than wear resistance of the material of the arm part 17 is used for the friction plates 46 and 47. Since a material having high wear resistance is heavy, the arm part 17 is heavy in a case in which the same material as the material of the friction plates 46 and 47 is used for the arm part 17.

As described above, the friction mechanism 50 generates a frictional force that cancels a difference between the positive rotational moment N1 and the negative rotational moment N2 acting on the arm part 17. Since the positive rotational moment N1 and the negative rotational moment N2 against the positive rotational moment N1 are increased with an increase in the weight of the arm part 17, a difference between the positive rotational moment N1 and the negative rotational moment N2 also tends to be increased an increase in the weight of the arm part 17. For this reason, since a difference between the positive rotational moment N1 and the negative rotational moment N2 is also reduced in a case in which a material lighter than the material of the friction plates 46 and 47 is used for the arm part 17, a frictional force generated by the friction mechanism 50 can be reduced.

Since the friction mechanism 50 is built in a portion of which a space is very limited, such as the pillar 18 of the arm part 17, there is a strong demand for making the friction mechanism 50 compact. Since a friction plate having a compact size has a small friction surface, it is difficult to generate a large frictional force by the compact friction plate in comparison with a friction plate that has a relatively large friction surface. For this reason, a reduction in the weight of the arm part 17 can allow the required performance of a frictional force, which is required for the friction mechanism 50 having a limitation of size, to be lowered. Accordingly, since a merit in terms of costs is improved, a reduction in the weight of the arm part 17 is very effective in a case in which the part 17 and the friction plates 46 and 47 are formed of separate members and the arm part 17 and the friction mechanism 50 are combined with each other.

Further, as the wear resistance of a material is increased, the weight of the material is increased. Accordingly, in a case in which the arm part 17 and the friction plates 46 and 47 are formed of separate members, the arm part 17 can be reduced in weight. A reduction in the weight of the arm part 17 also directly contributes to the improvement of operability of the arm part 17 and the mobility of the cart 11. Furthermore, since a material having high wear resistance is expensive, the limitation of a portion for which the material having high wear resistance is used also contributes to a reduction in costs.

Moreover, since the friction mechanism 50 uses the Belleville springs 61 as a biasing unit, the friction mechanism 50 generates a large reaction force with a compact size in comparison with a case in which a coil spring is used. As a result, a large frictional force can be generated. For this reason, the friction mechanism 50 is effective in a case in which the friction mechanism 50 is to be built in the pillar 18 of which a space is limited.

Further, the following effects are also obtained in a case in which the friction plates 46 and 47 having high wear resistance are combined with the Belleville springs 61. In comparison with a coil spring, a range in which the Belleville spring 61 can be displaced is narrow but the Belleville spring 61 can generate a large reaction force with small displacement. In other words, a change in the reaction force of the Belleville spring 61 is large at small displacement. For this reason, in a case in which the thicknesses of the friction plates 46 and 47 are changed due to the wear of the friction plates 46 and 47, a change in the reaction force of the Belleville springs 61 is increased in comparison with a coil spring. In a case in which the friction plates 46 and 47 having high wear resistance are used, wear is suppressed. As a result, the displacement of the Belleville springs 61 is also suppressed. Accordingly, a change in the reaction force of the Belleville springs 61 is suppressed.

An example in which the arm part 17 can be stopped at an arbitrary rotation position in the entire rotation range of the arm part 17 between the upper end position and the storage position has been described in this embodiment. However, the arm part 17 may not necessarily be stopped in the entire rotation range. For example, it is highly unlikely that the X-ray irradiation section 15 is used for imaging in a state in which the arm part 17 is in the storage position. For this reason, a rotation range, which is expected as a rotation range to be used for imaging, is set as a usable range in advance, and the arm part 17 may be stopped at an arbitrary rotation position in the set usable range. Even in this case, the storage position locking mechanism can be used to lock the arm part 17 at the storage position.

Furthermore, an example in which the gas springs 37 are used as a spring that generates negative rotational moment has been described in the above-mentioned embodiment, but springs other than the gas spring 37, such as a coil spring, may be used.

Modification Examples of Belleville Spring Unit

Figure 16:
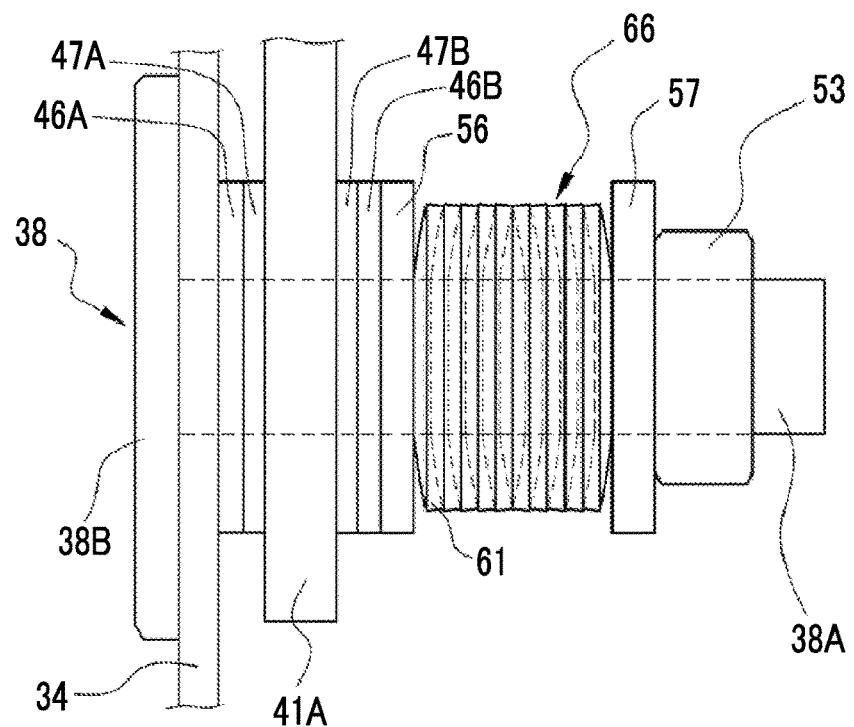
FIG. 16 shows a first modification example of a biasing unit in which the arrangement postures of Belleville springs are changed.

The arrangement postures of the Belleville springs in the Belleville spring unit can be modified in various ways. For example, a Belleville spring unit 66 shown in FIG. 16 includes ten Belleville springs 61 as in the Belleville spring unit 54 shown in FIG. 12, but the arrangement postures of five Belleville springs 61 corresponding to a left half and the arrangement postures of five Belleville springs 61 corresponding to a right half are reversed to those of the Belleville spring unit 54.

As in the Belleville spring unit 66, the arrangement postures of the Belleville springs 61, which are disposed at both ends, may be adapted so that the convex surfaces 61A face the outside. Of course, in terms of rotational moment around an axis and the dispersion of stress, it is preferable that the Belleville springs are disposed so that the concave surfaces 61B face the outside as shown in FIG. 12. Further, since at least one set of Belleville springs 61 having different arrangement postures is included even in a case in which the Belleville springs 61 are arranged in this way, an effect of reducing a spring constant is obtained. Furthermore, since the numbers of Belleville springs 61 having different arrangement postures are equal to each other and are five, respectively, uneven permanent deformation of the Belleville springs 61 can be prevented.

Figure 17:
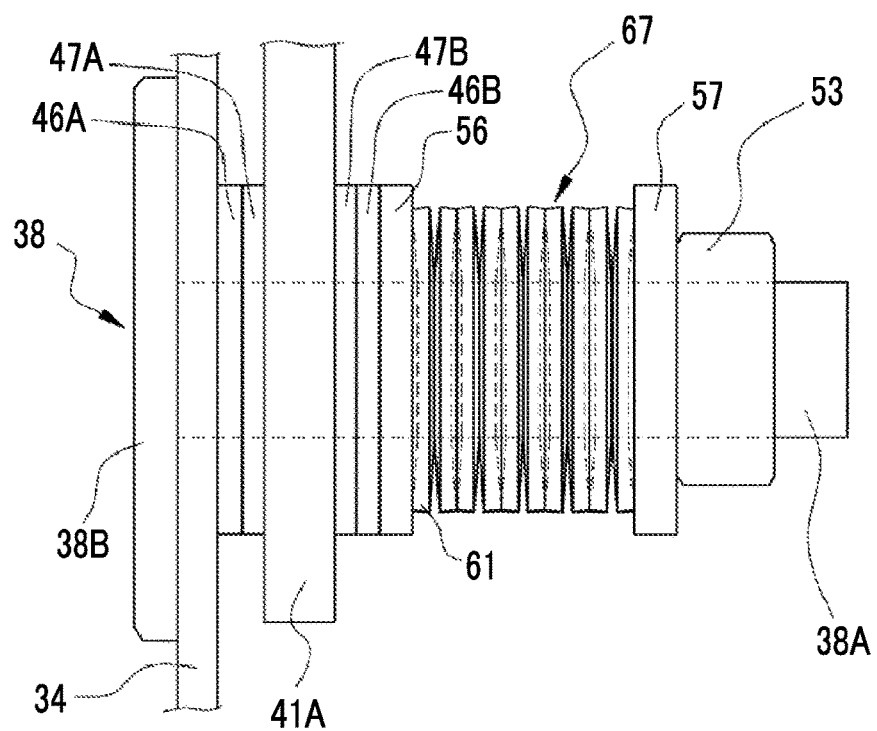
FIG. 17 shows a second modification example of the biasing unit in which the arrangement postures of Belleville springs are changed.

As in a Belleville spring unit 67 shown in FIG. 17, the Belleville springs may be arranged so that the arrangement postures of the Belleville springs are changed every Belleville spring. Even in this case, an effect of reducing a spring constant and an effect of preventing uneven permanent deformation of the Belleville springs 61 are obtained as in the Belleville spring unit 54 shown in FIG. 12 and the Belleville spring unit 66 shown in FIG. 16. Further, as in the Belleville spring unit 54 shown in FIG. 12, the Belleville spring unit 67 includes one set of Belleville springs 61 arranged so that the convex surfaces 61A face each other. Accordingly, it is easy to confirm the degree of tightening at the time of assembly. Furthermore, since Belleville springs 61 disposed at both ends of the Belleville spring unit 67 are arranged in a posture where the concave surface 61B faces the outside, an effect of increasing rotational moment around an axis and an effect of dispersing stress are obtained as in the Belleville spring unit 54 shown in FIG. 12.

Belleville springs have been used as a biasing unit in the above-mentioned examples, but springs other than the Belleville springs may be used and the biasing unit may be formed of a coil spring or the like. Of course, there are various merits in a case in which the Belleville springs are used as described above. Particularly, Belleville springs, which can generate a large reaction force with a compact size, are suitable to be used for the friction mechanism 50 of the cart 11 that needs to be built in a portion of which a space is limited, such as the pillar 18, and requires a large reaction force to stop the weighty arm part 17 including the X-ray irradiation section 15.

Second Embodiment

A second embodiment shown in FIGS. 18 to 23 is an embodiment in which storage portions for storing lubricating oil are provided on friction surfaces of friction plates 46 and 47. Lubricating oil, which is applied to the friction surfaces of the friction plates 46 and 47, deteriorates with time while the friction surfaces repeatedly slide on each other. In a case in which the storage portions are provided, new lubricating oil can be supplied to the friction surfaces.

Figure 18:
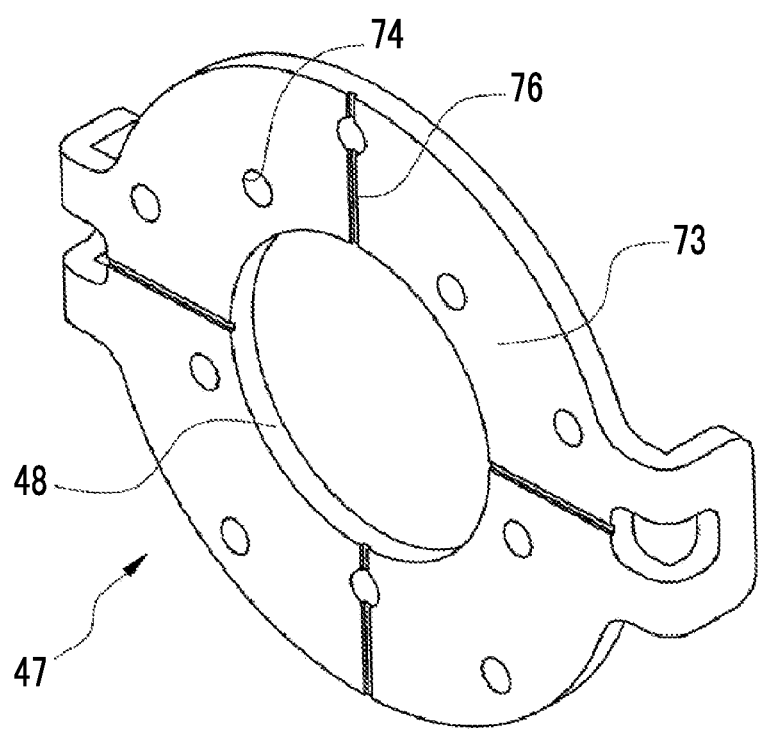
FIG. 18 is a perspective view of a rotating friction plate.
Figure 19:
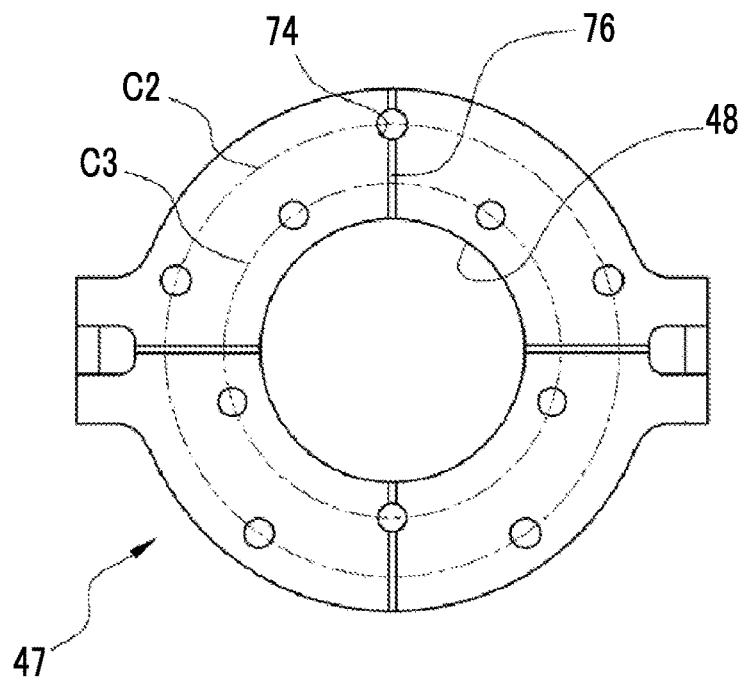
FIG. 19 is a plan view of the rotating friction plate.
Figure 20:
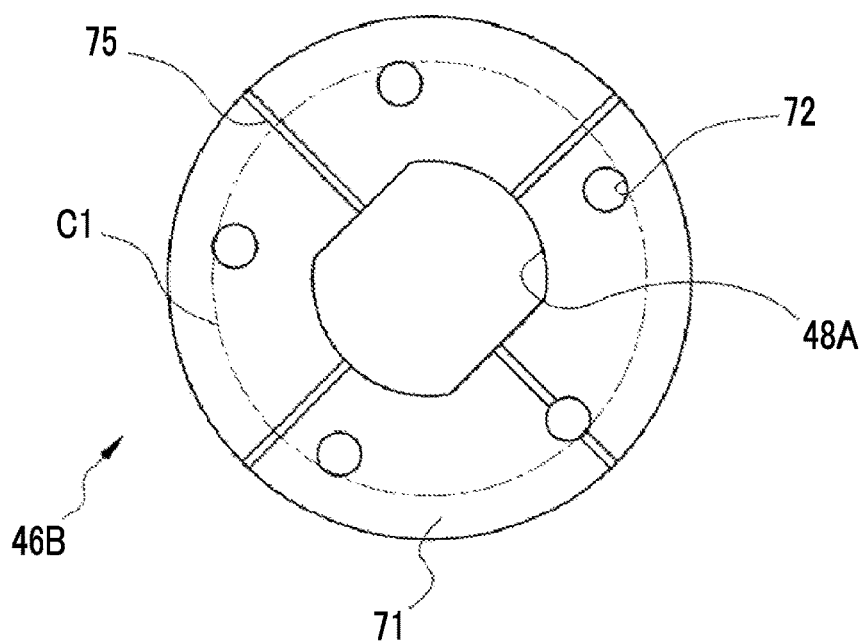
FIG. 20 is a plan view of a fixed friction plate.

In FIGS. 18 and 19, storage holes 74 are formed on a friction surface 73 of the friction plate 47 as the storage portions. As shown in FIG. 20, storage holes 72 are formed on a friction surface 71 of the friction plate 46 as the storage portion. The shape of each of the storage holes 72 and 74 is a circular shape.

A plurality of storage holes 72 are disposed on the friction surface 71 so as to be dispersed in the circumferential direction of the friction surface 71, and a plurality of storage holes 74 are disposed on the friction surface 73 so as to be dispersed in the circumferential direction of the friction surface 73. In a case in which the friction plate 47 is rotated and the friction surfaces 71 and 73 sliding on each other, the storage holes 72 and 74 of the respective friction surfaces 71 and 73 are moved with respect to each other in the circumferential direction. Accordingly, lubricating oil can be supplied to the friction surfaces 71 and 73 in the circumferential direction.

Since the storage holes are disposed so as to be dispersed in the circumferential direction, lubricating oil is easily spread over the entire circumference of each of the friction surfaces 71 and 73. Further, it is preferable that the arrangement pitches of the storage holes 72 and 74 in the circumferential direction are constant. Accordingly, the amount of lubricating oil to be supplied is likely to be uniform in the circumferential directions of the friction surfaces 71 and 73.

Furthermore, a plurality of grooves 76, which extend radially, are formed on the friction surface 73 of the friction plate 47. The groove 76 functions as a groove-shaped storage portion. Since the grooves 76 extend radially, lubricating oil can be supplied in the radial direction of the friction surface 73. Moreover, both ends of the groove 76 function as inlets that allow lubricating oil to enter the friction surface 73 from the outer peripheral side of the friction plate 47 and the inner peripheral side where the shaft hole 48 is formed. Grooves 75 are also formed on the friction plate 46 as shown in FIG. 20 and the grooves 75 also have the same function as the grooves 76.

Figure 21:
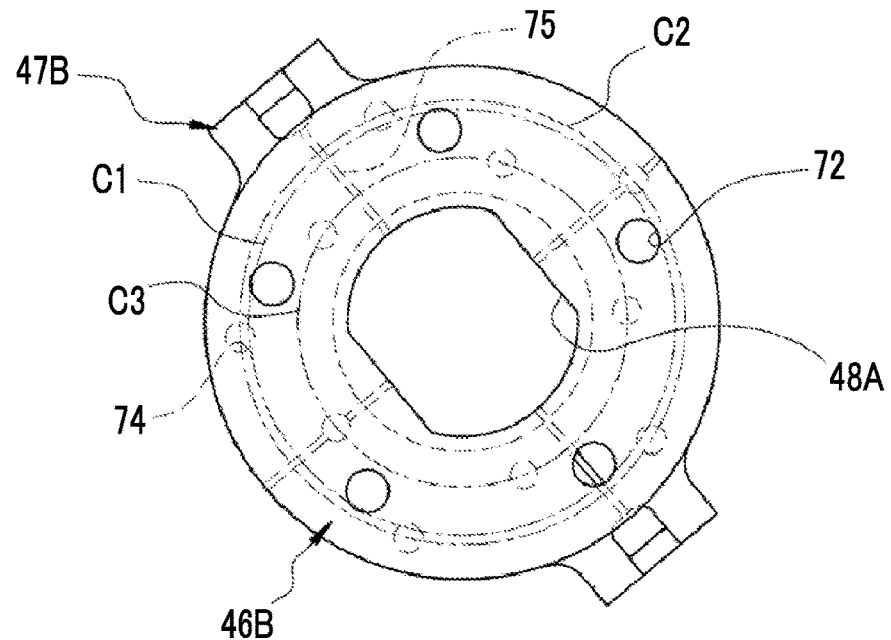
FIG. 21 is a diagram illustrating the position of a storage portion in a case in which a set of friction plates face each other.

FIG. 21 shows a state in which the friction plate 46 and the friction plate 47 face each other and the friction surfaces 71 and 73 are in contact with each other. As shown in FIG. 21, the storage holes 72 and 74 are disposed so as to be dispersed in the radial direction. More specifically, as shown in FIG. 20, the storage holes 72 of the friction plate 46 are disposed so as to be dispersed on a first circumference C1 that faces the outer peripheral edge 61C of the Belleville spring 61.

Figure 22:
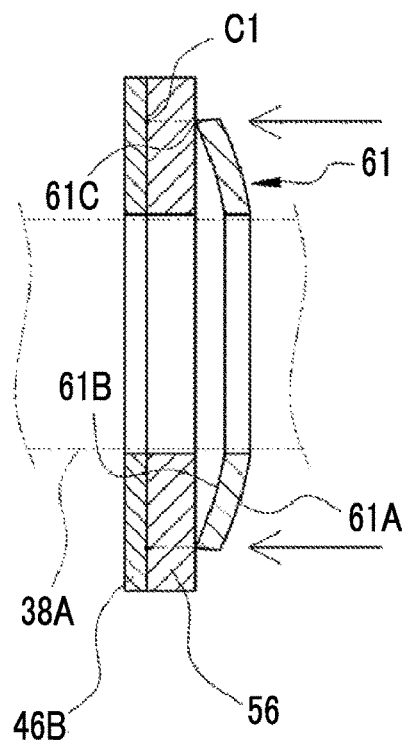
FIG. 22 is a diagram showing a first circumference C1 of a friction surface.

As shown in FIG. 22, the friction plate 46 is pressed from the Belleville spring 61 through the cushioning plate 56. In a case in which the concave surface 61B of the Belleville spring 61 faces the cushioning plate 56 as described in FIG. 12 of first embodiment, the Belleville spring 61 generates a pressing force applied to the cushioning plate 56 at the outer peripheral edge 61C. The Belleville spring 61 presses the friction plate 46 through the cushioning plate 56. In this case, a pressing force received from the Belleville springs 61 is relatively increased at a position facing the outer peripheral edge 61C even on the friction surface 71 of the friction plate 46. A position facing the outer peripheral edge 61C on the friction surface 71 corresponds to the first circumference C1 around the axis of the rotation axis AX2 as a center.

A portion positioned on the first circumference C1 where the pressing force is large as described above is a portion at which lubricating oil is most needed. However, since the pressing force is large on the first circumference C1 as shown in FIG. 22 by arrows, lubricating oil is likely to escape to the outer peripheral side or the inner peripheral side. Accordingly, as shown in FIG. 20, the storage holes 72 are disposed on the friction surface 71 of the friction plate 46 so as to be dispersed on the first circumference C1. Therefore, new lubricating oil can be supplied to a portion at which lubricating oil is most needed from the storage holes 72. Here, the portion positioned on the first circumference C1 means a position that overlaps the first circumference C1. For this reason, some storage holes 72 and the first circumference C1 may overlap each other.

Further, as shown in FIG. 19, the storage holes 74 are disposed on a second circumference C2 and a third circumference C3 on the friction surface 73 of the friction plate 47. As shown in FIG. 21, the second circumference C2 and the third circumference C3 are concentric circles having diameters different from the diameter of the first circumference C1. The second circumference C2 is a circumference that has a diameter larger than the diameter of the first circumference C1 and is positioned outside the first circumference C1. The third circumference C3 is a circumference that has a diameter smaller than the diameter of the first circumference C1 and is positioned inside the first circumference C1. Since the storage holes 72 and 74 are disposed on the plurality of concentric circles having different diameters as described above, the storage holes 72 and 74 can be disposed so as to be dispersed in the radial direction.

Furthermore, the storage holes 72 are disposed on the first circumference C1, and the storage holes 74 are disposed on the second circumference C2 and the third circumference C3 that are positioned outside and inside the first circumference C1 in the radial direction, respectively. For this reason, lubricating oil can be supplied to the portion, which is positioned on the first circumference C1 and at which lubricating oil is most needed, from the inside and outside. Here, the storage holes 72 disposed on the first circumference C1 correspond to first storage portions, the storage holes 74 disposed on the second circumference C2 correspond to second storage portions, and the storage holes 74 disposed on the third circumference C3 correspond to third storage portions.

As described above, the friction surface 71 of one friction plate 46 of one set of friction plates 46 and 47 is provided with the storage holes 72 corresponding to the first storage portions and the friction surface 73 of the other friction plate 47 thereof is provided with the storage holes 74 corresponding to the second and third storage portions. Since the storage portions are formed by the cutting of the friction plate, it is preferable that the number of the storage portions is small in terms of the strength of the friction plate. For this reason, in a case in which the storage holes 72 and 74 are dispersed on each of one set of the friction plates 46 and 47 as in this embodiment, a reduction in the strength of one friction plate can be suppressed in comparison with a case in which one friction plate is provided with all the storage portions.

Further, the size of each of the storage holes 72 disposed on the first circumference C1 is larger than the size of each of the storage holes 74 disposed on the second circumference C2 and the third circumference C3. Since the contact area of the friction surface is reduced by an area corresponding to the storage holes in a case in which the storage holes are formed on the friction surface, it is preferable that the number of the storage portions is as small as possible in terms of suppressing a reduction in contact area. Since the storage holes 72 corresponding to the portion at which lubricating oil is most needed are large and the storage holes 74 corresponding to other portions are small, it is possible to suppress a reduction in contact area while ensuring the amount of required lubricating oil.

Furthermore, as shown in FIG. 19, the plurality of storage holes 74 disposed on the second circumference C2 and the plurality of storage holes 74 disposed on the third circumference C3 are arranged on the friction plate 47 at regular intervals in the circumferential direction. Moreover, the plurality of storage holes 74 disposed on the second circumference C2 and the plurality of storage holes 74 disposed on the third circumference C3 are disposed in a state in which phases of the storage holes are shifted from each other. That is, since each of the storage holes 74 disposed on the second circumference C2 is disposed between the two storage holes 74, which are disposed on the third circumference C3, in the circumferential direction, the positions of the storage holes in the circumferential direction are shifted from each other. Since the storage holes are disposed in this way, lubricating oil is likely to be supplied in the circumferential direction in the first circumference C1 even though the rotation angle of the friction plate 47 caused by the rotation of the arm part 17 is small.

In this embodiment, the circular storage holes 72 and 74 and the grooves 76 have been described as the storage portion by way of example. However, the shape of the storage portion may be any shape, and may be, for example, the shape of an elongate hole including an oval. Of course, there is a merit that the storage portion is easily formed in a case in which the storage portion has a circular shape or the shape of a groove. Further, the circular storage holes 74 and the grooves 76 have been mixed, but only one kind of the circular storage holes 74 and the grooves 76 may be provided. The number of the storage portions (storage holes, grooves) can be appropriately changed in consideration of the area of the friction surface and the like.

Figure 23:
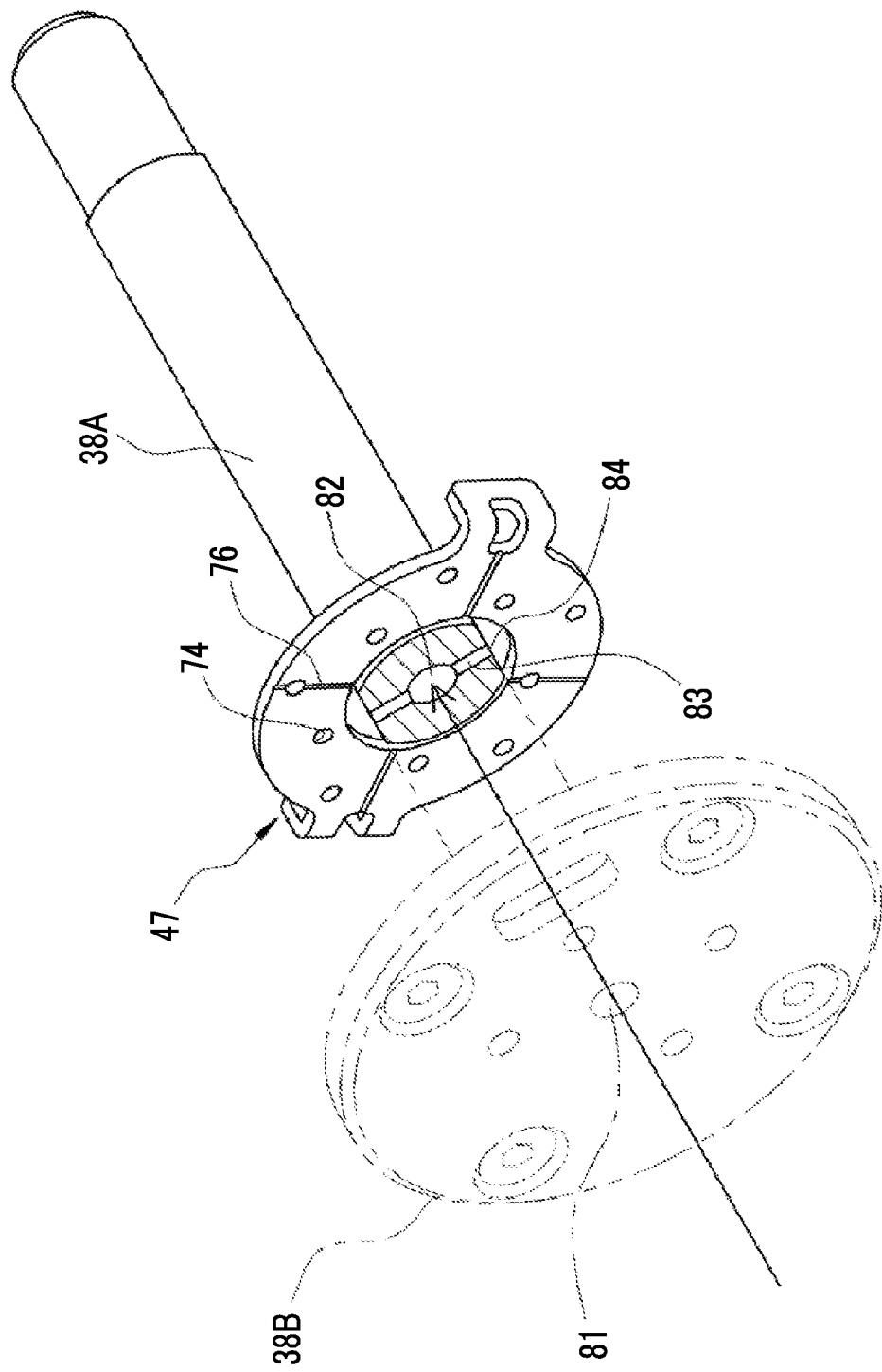
FIG. 23 is a diagram showing a supply passage that supplies lubricating oil.

Furthermore, lubricating oil may be adapted to be capable of being supplied to the friction surfaces 71 and 73 of the friction plates 46 and 47 in a state in which the friction mechanism 50 including the friction plates 46 and 47 and the normal force generating section 51 is assembled as shown in FIG. 23. In the state in which the friction mechanism 50 is assembled, the shaft portion 38A of the shaft member 38 is inserted into the shaft hole 48 that is an opening formed at the center of the friction plates 46 and 47.

A supply passage for supplying lubricating oil to the friction surfaces 71 and 73 is provided in the shaft portion 38A. The supply passage includes an inlet 81 that is formed at the large-diameter portion 38B provided at one end of the shaft member 38, a first supply passage 82 that extends from the inlet 81 in an axial direction, and a second supply passage 83 that extends from the first supply passage 82 to an outer peripheral surface of the shaft portion 38A and is connected to an outlet 84 formed on the outer peripheral surface at mounting positions of the friction plates 46 and 47 in the axial direction. The outlet 84 faces the inner peripheries of the shaft holes 48 of the friction plates 46 and 47.

In a case in which the exterior member of the second pillar part 18B is removed at the time of the maintenance of the cart 11, the large-diameter portion 38B is exposed to the outside. Lubricating oil is pressurized from the inlet 81 and is injected into the first supply passage 82. The pressurized lubricating oil is ejected from the outlet 84 through the first supply passage 82 and the second supply passage 83. Then, the ejected lubricating oil passes through a gap between the outer periphery of the shaft portion 38A and the inner periphery of the shaft hole 48 of the friction plate 47, and enters the friction surface 73 through the grooves 76 of the friction plate 47. Since lubricating oil can be supplied in this way in a state in which the friction mechanism 50 is assembled, it is easy to perform maintenance.

A combination of the X-ray irradiation section 15 and the electronic cassette has been used in the respective embodiments of the invention, but a combination of the X-ray irradiation section 15 and a film cassette, which uses an X-ray film as an image recording medium, used instead of the electronic cassette may be used.

Further, the invention can also be applied to a radiation irradiator that applies radiation, such as a γ-ray, other than an X-ray. Furthermore, the invention is not limited to each of the embodiments, and may have appropriate modifications, such as combination of the respective embodiments, without departing from the scope of the invention.

EXPLANATION OF REFERENCES

2: X-ray imaging system
11: cart
12: electronic cassette
13: bed
14: carriage part
15: X-ray irradiation section
15A: radiation source unit
15B: irradiation field limiter
15C: X-ray tube
16: body part
17: arm part
17A: free end
17B: base end
18: pillar 18A: first pillar part
18B: second pillar part
18C: grip portion
19: handle
21: operation panel
23: irradiation switch
24: placement surface
28: cassette storage portion
29F: front wheels
29R: rear wheels
30: total
31: holding portion
32: mounting part
32A: joint
33: frame member
34: frame plate
36: back plate
37: gas spring
37A: end portion
37B: end portion
38: shaft member
38A: shaft portion
38B: large-diameter portion
41A, 41B: side plate
42: connecting portion
43: slit
44: screw
45: shaft hole
46: friction plate (fixed friction plate)
46A, 46B: friction plate (fixed friction plate)
47: friction plate (rotating friction plate)
47A, 47B: friction plate (fixed friction plate)
48: shaft hole
48A: shaft hole
50: friction mechanism
51: normal force generating section
52: insertion hole
53: nut
54, 66, 67: Belleville spring unit
56, 57: cushioning plate
58: case
58A: upper case member
58B: lower case member
61: Belleville spring
61A: convex surface
61B: concave surface
61C: outer peripheral edge
61D: shaft hole
71, 73: friction surface
72, 74: storage hole
73, 71: friction surface
75, 76: groove
81: inlet
82: first supply passage
83: second supply passage
84: outlet
AX1: rotation axis
AX2: rotation axis
AX3: rotation axis
AX4: rotation axis
C1: first circumference
C2: second circumference
C3: third circumference
H: subject (patient)
N1: rotational moment
N2: rotational moment
ST: medical staff T01, T02, T11, T12: thickness
W0: width
W1: width
ΔF: frictional force

What is claimed is:

1. A mobile radiation generator comprising:
a carriage part that includes wheels;
a pillar that is provided on the carriage part;
an arm part where an irradiation section is mounted on a free end and a base end is rotatably supported by the pillar, the position of the irradiation section in a vertical direction being changed in a case in which the arm part is rotated while the base end serves as a base point;
a spring that generates negative rotational moment in a negative direction where the irradiation section is displaced upward against positive rotational moment that acts on the arm part in a positive direction due to own weight of the arm part and the irradiation section in a case in which a direction where the irradiation section is displaced downward in the vertical direction is prescribed as the positive direction;
a friction mechanism that generates a frictional force acting in a direction opposite to a direction where the arm part is to be rotated due to a difference between the positive rotational moment and the negative rotational moment and cancelling a difference between the positive rotational moment and the negative rotational moment in a case in which the magnitude of the positive rotational moment and the magnitude of the negative rotational moment are different from each other,
wherein the friction mechanism includes
at least one set of friction plates that includes a friction plate rotated with the rotation of the arm part and a friction plate disposed so as to face the friction plate to be rotated and not rotated regardless of the rotation of the arm part and generates the frictional force by contact between friction surfaces of the respective friction plates, and
a normal force generating section that includes a biasing unit and a plurality of nuts, wherein the biasing unit applies a biasing force in a direction where the friction surfaces of the set of friction plates are pressed against each other and generates a normal force on the friction surfaces,
wherein the friction plates, the biasing unit and the plurality of nuts are disposed along a rotation axis of the arm part, and the biasing unit is disposed closer to the friction plates than the plurality of nuts, and
wherein the pillar comprises a pair of frame plates that are disposed at intervals in a width direction, and the friction mechanism is all received in the interval between the pair of frame plates of the frame member at a position that the frame member is connected to the arm part; and
a single shaft member inserted through the pair of frame plates and the friction mechanism, wherein the friction mechanism is fixed in the interval between the pair of frame plates through the single shaft member connected therebetween.

2. The mobile radiation generator according to claim 1, wherein separate materials are used for the arm part and the friction plate, and a material having wear resistance higher than wear resistance of the arm part is used for the friction plate.

3. The mobile radiation generator according to claim 1, wherein the friction plates of which the friction surfaces are in contact with each other are made of the same material.

4. The mobile radiation generator according to claim 1, wherein the biasing unit includes at least one disc-shaped Belleville spring of which one surface is a convex surface and the other surface is a concave surface.

5. The mobile radiation generator according to claim 4, wherein the biasing unit is a Belleville spring unit that includes a plurality of the Belleville springs arranged so as to be stacked in an axial direction about which the friction plates are rotated.

6. The mobile radiation generator according to claim 5, wherein the Belleville spring unit includes at least one set of Belleville springs having different arrangement postures, the arrangement posture meaning orientation of the convex surface or the concave surface.

7. The mobile radiation generator according to claim 5, wherein the Belleville spring unit includes at least one set of Belleville springs arranged so that the convex surfaces face each other.

8. The mobile radiation generator according to claim 5, wherein the Belleville springs, which are disposed at both ends of the Belleville spring unit, are arranged in a posture where the concave surface faces the outside.

9. The mobile radiation generator according to claim 5, wherein the plurality of Belleville springs having different arrangement postures are mixed in the Belleville spring unit, and
the numbers of the Belleville springs having the respective arrangement postures are equal to each other.

10. The mobile radiation generator according to claim 5, wherein a cushioning member is interposed between the Belleville spring unit and the friction plate, and the Belleville spring unit applies the biasing force to the friction plate through the cushioning member.

11. The mobile radiation generator according to claim 1, wherein lubricating oil is used as lubricant between the friction surfaces of the friction plates.

12. The mobile radiation generator according to claim 11, wherein the lubricating oil is lithium soap grease.

13. The mobile radiation generator according to claim 11, wherein storage portions in which the lubricating oil is stored are formed on the friction surface of at least one friction plate of one set of friction plates.

14. The mobile radiation generator according to claim 13, wherein the storage portions are disposed so as to be dispersed in a circumferential direction of the friction surface.

15. The mobile radiation generator according to claim 14, wherein the biasing unit is a Belleville spring unit that includes at least one disc-shaped Belleville spring of which one surface includes a convex surface and the other surface includes a concave surface and includes a plurality of the Belleville springs arranged so as to be stacked in an axial direction about which the friction plates are rotated, and
the Belleville spring, which is disposed on an end face of the Belleville spring unit facing the friction plate, is arranged in a posture where the concave surface faces the friction plate.

16. The mobile radiation generator according to claim 15, wherein the storage portions are disposed so as to be dispersed on a first circumference facing an outer peripheral edge of the Belleville spring.

17. The mobile radiation generator according to claim 16, wherein the storage portions are also disposed so as to be dispersed on circumferences of a plurality of concentric circles having diameters different from the diameter of the first circumference.

18. The mobile radiation generator according to claim 17, wherein the plurality of concentric circles includes a second circumference that is positioned outside the first circumference and a third circumference that is positioned inside the first circumference.

19. The mobile radiation generator according to claim 18, wherein first storage portions, which are storage portions disposed on the first circumference, are provided on the friction surface of one friction plate of one set of friction plates, and
second storage portions that are storage portions disposed on the second circumference and third storage portions that are storage portions disposed on the third circumference are provided on the friction surface of the other friction plate thereof.

20. The mobile radiation generator according to claim 19, on the friction plate where the storage portions are disposed on the second circumference and the third circumference,
the plurality of storage portions, which are disposed so as to be dispersed on each of the second circumference and the third circumference, are arranged at regular intervals in the circumferential direction, and
the plurality of storage portions disposed on the second circumference and the plurality of storage portions disposed on the third circumference are disposed in a state in which phases of the storage portions are shifted from each other in the circumferential direction.

21. The mobile radiation generator according to claim 18, wherein the size of the storage portion disposed on the first circumference is larger than the size of the storage portion disposed on the second circumference and the size of the storage portion disposed on the third circumference.

22. The mobile radiation generator according to claim 13, wherein the shape of the storage portion is at least one of a circular shape, the shape of an elongate hole, or the shape of a groove.

23. The mobile radiation generator according to claim 22, wherein the storage portions are grooves, the grooves are arranged radially on the friction surface.

24. The mobile radiation generator according to claim 23, wherein
the single shaft member is inserted into an opening formed in the friction plate,
wherein a supply passage for supplying the lubricating oil to the friction surface is provided in the single shaft member, and
the supply passage includes an inlet that is formed at one end of the single shaft member, a first supply passage that extends from the inlet in an axial direction of the single shaft member, and a second supply passage that extends from the first supply passage to an outer peripheral surface of the single shaft member and is connected to an outlet formed on the outer peripheral surface at a mounting position of the friction plate in the axial direction.

* * * * *